United States Patent [19]

Burckhardt et al.

[11] Patent Number: 5,215,570
[45] Date of Patent: Jun. 1, 1993

[54] SULFAMOYLPHENYLUREAS

[75] Inventors: Urs Burckhardt, Basel, Switzerland; Raafat Soliman, Alexandria, Egypt; Werner Töpfl, Dornach; Hans-Rudolf Waespe, Allschwil, both of Switzerland

[73] Assignee: Ciba-Geigy Corporation, Ardsley, N.Y.

[21] Appl. No.: 637,097

[22] Filed: Jan. 3, 1991

Related U.S. Application Data

[63] Continuation-in-part of Ser. No. 422,863, Oct. 17, 1989, abandoned.

[30] Foreign Application Priority Data

Oct. 20, 1988 [CH] Switzerland ............... 3914/88-2

[51] Int. Cl.$^5$ ............................................. A01N 31/00
[52] U.S. Cl. ........................................ 504/104; 564/49; 504/112; 504/108; 504/110; 504/109; 504/105; 504/107
[58] Field of Search .................... 564/49; 71/98

[56] References Cited

U.S. PATENT DOCUMENTS

| | | | |
|---|---|---|---|
| 3,119,682 | 1/1964 | Martin et al. | 71/98 |
| 3,600,436 | 5/1972 | Scherer et al. | 564/49 |
| 3,775,403 | 11/1973 | Shen et al. | 564/49 |
| 4,127,405 | 11/1978 | Levitt . | |
| 4,260,411 | 4/1981 | Yoshida et al. | 71/88 |
| 4,618,361 | 10/1986 | Moser . | |

FOREIGN PATENT DOCUMENTS

| | | |
|---|---|---|
| 0007687 | 2/1980 | European Pat. Off. . |
| 0030142 | 6/1981 | European Pat. Off. . |
| 0044807 | 1/1982 | European Pat. Off. . |
| 0044808 | 1/1982 | European Pat. Off. . |
| 0051466 | 5/1982 | European Pat. Off. . |
| 0070802 | 1/1983 | European Pat. Off. . |
| 0084020 | 7/1983 | European Pat. Off. . |
| 0087780 | 9/1983 | European Pat. Off. . |
| 0102925 | 3/1984 | European Pat. Off. . |
| 0108708 | 5/1984 | European Pat. Off. . |
| 0120814 | 10/1984 | European Pat. Off. . |
| 0122231 | 10/1984 | European Pat. Off. . |
| 0136061 | 4/1985 | European Pat. Off. . |
| 0147365 | 7/1985 | European Pat. Off. . |
| 0184385 | 6/1986 | European Pat. Off. . |
| 0206995 | 12/1986 | European Pat. Off. . |
| 0237292 | 9/1987 | European Pat. Off. . |
| 0243313 | 10/1987 | European Pat. Off. . |
| 2402983 | 8/1974 | Fed. Rep. of Germany . |
| 2828265 | 1/1980 | Fed. Rep. of Germany . |
| 2828293 | 1/1980 | Fed. Rep. of Germany . |
| 1277557 | 6/1972 | United Kingdom . |

Primary Examiner—C. Warren Ivy
Assistant Examiner—Celia Chang
Attorney, Agent, or Firm—Edward McC. Roberts

[57] ABSTRACT

The N-acylsulfamoylphenylureas of formula I below are suitable as counter-agents (antidotes or safeners) for protecting cultivated plants from the phytotoxic action of herbicides. Suitable crops are preferably cereals, soybeans, sorghum, maize and rice, and suitable herbicides are sulfonylureas, chloroacetanilides and aryloxyphenoxypropionic acid derivatives.

The N-acylsulfamoylphenylureas have the formula I

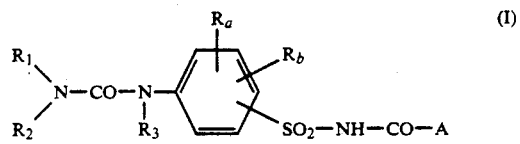

wherein A is a radical selected from the group

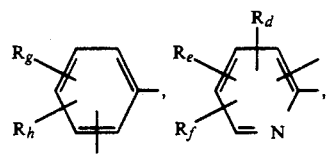

(Abstract continued on next page.)

-continued

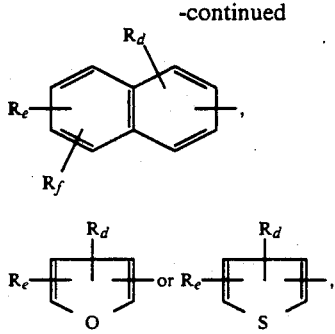

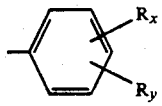

or $C_1$–$C_4$alkyl substituted by $C_1$–$C_4$alkoxy or by

$R_1$ is $C_1$–$C_4$-alkoxy or each of $R_1$ and $R_2$, independently of the other, is hydrogen, $C_1$–$C_8$alkyl, $C_3$–$C_8$cycloalkyl, $C_3$–$C_6$alkenyl, $C_3$–$C_6$alkynyl, or $R_1$ and $R_2$ together form a $C_4$–$C_6$alkylene bridge, or a $C_4$–$C_6$alkylene bridge interrupted by oxygen, sulfur, SO, SO$_2$, NH or by —N($C_1$–$C_4$alkyl)-, $R_3$ is hydrogen or $C_1$–$C_4$alkyl, $R_a$ to $R_h$, $R_x$ and $R_y$ are as defined in the disclosure.

36 Claims, No Drawings

SULFAMOYLPHENYLUREAS

CROSS REFERENCE TO RELATED APPLICATIONS

This is a continuation-in-part of application Ser. No. 422,863 filed on Oct. 17, 1989 now abandoned.

The present invention relates to novel N-acylsulfamoylphenylureas that are suitable for protecting cultivated plants from the phytotoxic action of acylcyclohexanedione herbicides, sulfonylurea herbicides, chloroacetanilide herbicides and aryloxyphenoxypropionic acid herbicides. The invention relates also to the preparation of the novel compounds and to their use for the protection of cultivated plants. The invention relates also to compositions containing the novel active ingredient and to herbicidal compositions that contain a combination of herbicide and counter-agent, and to corresponding methods of weed control. Finally, the invention relates also to the seeds of cultivated plants protected against herbicidal action by treatment with N-acylsulfamoylphenylureas.

It is known that herbicides belonging to the classes of the sulfonylureas, haloacetanilides and aryloxyphenoxypropionic acid derivatives, when employed in an effective concentration, occasionally also damage cultivated plants to a certain extent in addition to the weeds that are to be controlled. Overdoses are often applied unintentionally and accidentally when edge zones overlap during stripwise spraying, either as a result of wind or as a result of incorrect judgement of the effective width of the spraying apparatus. The climatic conditions or the nature of the soil may be such that the concentration of herbicide recommended for normal conditions acts as an overdose. The quality of the seeds may also be a factor in the tolerance of the herbicide. To counteract this problem, various substances have already been proposed which are able specifically to antagonise the harmful action of the herbicide on the cultivated plant, i.e. to protect the cultivated plant without noticeably influencing the herbicidal action on the weeds to be controlled. However, it has been found that the proposed counter-agents often have very species-specific activity both with respect to the cultivated plants and with respect to the herbicide and also, in some cases, contingent on the mode of application, i.e. a specific counter-agent is often suitable only for a specific cultivated plant and a few classes of herbicide.

For example, British Patent Specification 1 277 557 describes the treatment of seeds or shoots of wheat and sorghum with certain oxamic acid esters and amides for protection against attack by "ALACHLOR" (N-methoxymethyl-N-chloroacetyl-2,6-diethylaniline).

U.S. Pat. No. 4,618,361 discloses benzoxazine derivatives having a protective action against the herbicidal action of haloacetanilides and sulfonylureas. For protection against sulfonylurea herbicides EP-A-122 231 proposes benzoyloxime ether and EP-A-147 365 proposes phenylglyoxylic acid nitrile oxime, naphthalenedicarboxylic acid anhydride, a thiazolecarboxylic acid ester and dichloroacetamides as counter-agents. Furthermore, according to DE-OS 2 402 983 maize plants can be effectively protected against damage by chloroacetanilides by adding an N-disubstituted dichloroacetamide to the soil as counter-agent. Such compounds are used according to DE-OS 2 828 265 and 2 828 293 also as antidotes against herbicidal acetanilides.

It has surprisingly now been found that a group of N-acylsulfamoylphenylureas are eminently suitable for protecting cultivated plants against the damaging effect of sulfonylurea herbicides, chloroacetanilide herbicides or aryloxyphenoxypropionic acid herbicides. These N-acylsulfamoylphenylureas are therefore referred to in the following text also as "counter-agents", "antidotes" or "safeners".

The novel N-acylsulfamoylphenylureas proposed according to the invention have the general formula I

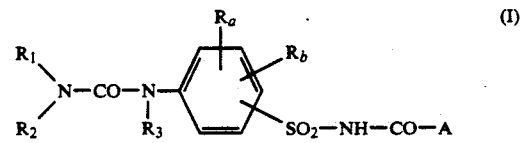

wherein A is a radical selected from the group

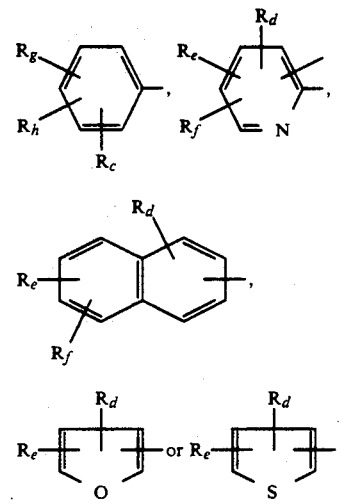

$R_1$ is $C_1$–$C_4$-alkoxy or each of $R_1$ and $R_2$, independently of the other, is hydrogen, $C_1$–$C_8$alkyl, $C_3$–$C_8$cycloalkyl, $C_3$–$C_6$alkenyl, $C_3$–$C_6$alkynyl,

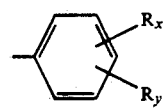

or $C_1$–$C_4$alkyl substituted by $C_1$–$C_4$alkoxy or by

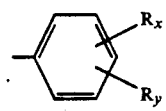

or $R_1$ and $R_2$ together form a $C_4$–$C_6$alkylene bridge, or a $C_4$–$C_6$alkylene bridge interrupted by oxygen, sulfur, SO, $SO_2$, NH or by —N($C_1$–$C_4$alkyl)-, $R_3$ is hydrogen or $C_1$–$C_4$alkyl, $R_a$ is hydrogen, halogen, cyano, trifluoromethyl, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$, —CONR$_k$R$_m$, —COR$_n$, —SO$_2$NR$_k$R$_m$, —OSO$_2$—$C_1$–$C_4$alkyl, $R_g$ is a hydrogen, halogen, cyano, nitro, $C_1$–$C_4$alkyl, $C_1$–$C_4$haloalkyl, $C_1$–$C_4$alkylthio, $C_1$–$C_4$alkylsulfinyl, $C_1$–$C_4$alkylsulfonyl, —COOR$_j$, —CONR$_k$R$_m$, —COR$_n$, —SO$_2$NR$_k$R$_m$ or —OSO$_2$—C$_1$-C$_4$alkyl, C$_1$-C$_6$alkoxy, or C$_1$-C$_6$alkoxy substituted by C$_1$-C$_4$-alkoxy or halogen, C$_3$-C$_6$alkenyloxy, or C$_3$-C$_6$alkenyloxy substituted by halogen, or C$_3$-C$_6$-alkynyloxy, or R$_a$ and R$_b$ together form a C$_3$-C$_4$alkylene bridge, which can be substituted by halogen or by C$_1$-C$_4$alkyl, or a C$_3$-C$_4$or alkenylene bridge, which can be substituted by halogen or by C$_1$-C$_4$alkyl, or a C$_4$alkadienylene bridge which can be substituted by halogen or by C$_1$-C$_4$alkyl, each of R$_b$ and R$_h$, independently of the other, is hydrogen, halogen, C$_1$-C$_4$alkyl, trifluoromethyl, C$_1$-C$_6$-alkoxy, C$_1$-C$_6$-alkylthio or —COOR$_j$, R$_c$ is hydrogen, halogen, nitro, C$_1$-C$_4$alkyl or methoxy, R$_d$ is hydrogen, halogen, nitro, C$_1$-C$_4$alkyl, C$_1$-C$_4$alkoxy, C$_1$-C$_4$alkylthio, C$_1$-C$_4$alkylsulfinyl, C$_1$-C$_4$alkylsulfonyl, —COOR$_j$ or CONR$_k$R$_m$, R$_e$ is hydrogen, halogen, C$_1$-C$_4$alkyl, —COOR$_j$, trifluoromethyl or methoxy, or R$_d$ and R$_e$ together form a C$_3$-C$_4$alkylene bridge, R$_f$ is hydrogen, halogen or C$_1$-C$_4$alkyl, each of R$_x$ and R$_y$, independently of the other, is hydrogen, halogen, C$_1$-C$_4$alkyl, C$_1$-C$_4$alkoxy, C$_1$-C$_4$alkylthio, —COOR$_4$, trifluoromethyl, nitro or cyano, each of R$_j$, R$_k$ and R$_m$, independently of the others, is hydrogen or C$_1$-C$_4$alkyl, R$_k$ and R$_m$ together form a C$_4$-C$_6$alkylene bridge, or a C$_4$-C$_6$alkylene bridge interrupted by oxygen, NH or by —N(C$_1$-C$_4$alkyl)-, and R$_n$ is C$_1$-C$_4$alkyl, phenyl, or phenyl substituted by halogen, C$_1$-C$_4$alkyl, methoxy, nitro or by trifluoromethyl.

In the definitions, halogen is to be understood as being fluorine, chlorine, bromine and iodine, but preferably fluorine, chlorine and bromine, especially chlorine. In general, haloalkyl is chloromethyl, fluoromethyl, difluoromethyl, trifluoromethyl, 2-chloroethyl, 2,2,2-trifluoroethyl, 1,1,2,2-tetrafluoroethyl, pentafluoroethyl, 3,3,3-trifluoropropyl, 2,3-dichloropropyl, 1,1,2,3,3,3-hexafluoropropyl, but in particular chloromethyl and trifluoromethyl.

Alkyl in the definitions is to be understood as being straight-chain or branched alkyl, for example methyl, ethyl, n-propyl, isopropyl or the four butyl isomers. Longer chain alkyl groups include the isomers of pentyl, hexyl, heptyl or octyl, the unbranched chains being preferred in each case. Alkoxy is to be understood as being: methoxy, ethoxy, n-propoxy, isopropoxy or the four isomeric butoxy radicals, but especially methoxy, ethoxy or isopropoxy. Alkyl substituted by alkoxy is preferably methoxymethyl, ethoxymethyl, methoxyethyl or ethoxyethyl, but especially methoxyethyl. Alkyl substituted by unsubstituted or substituted phenyl is preferably derivatives of phenylethyl or benzyl. C$_3$-C$_6$alkenyl and C$_3$-C$_6$alkynyl radicals in the definition of R$_1$ and R$_2$ are distinguished by being bonded via a saturated carbon atom to the nitrogen atom carrying them. Typical alkenyl and alkynyl radicals are allyl, 2-butenyl, methallyl, 3-butenyl, propargyl, 2-butynyl, 3-butynyl or 2-pentenyl. Examples of cycloalkyl are cyclopropyl, cyclopentyl, cyclohexyl and cycloheptyl, but preferably cyclopentyl and cyclohexyl. Heterocycles that are formed by R$_1$ and R$_2$ or R$_5$ and R$_6$ together with the nitrogen atom carrying them are pyrrolidine, piperidine, pyrazolidine, imidazolidine, oxazolidine, thiazolidine, morpholine, thiomorpholine, piperazine or hexahydroazepine and, in the case of sulfur-containing rings, the oxidation products thereof. In alkylthio, alkylsulfinyl or alkylsulfonyl, alkyl has the specific meanings listed above.

When R$_a$ and R$_b$ together form a C$_3$-C$_4$alkylene bridge, C$_3$-C$_4$alkenylene bridge or C$_4$alkadienylene bridge, each of which can be substituted by halogen or by C$_1$-C$_4$alkyl, then, together with the phenyl ring to which the bridge is bonded, dinuclear systems are formed, for example 1,2,3,4-tetrahydronaphthalene, 1-chloro-2-methyl-3,4-dihydronaphthalene, indane, 1,2-dihydronaphthalene, indene, naphthalene, 2-methylnaphthalene, 1-n-butylnaphthalene, 2-ethylnaphthalene or 1-chloronaphthalene.

When the substituents R$_d$ and R$_e$ together form a C$_3$-C$_4$alkylene bridge, then, together with the ring system to which they are bonded, polynuclear systems are formed, for example 2,3-tetramethylenethiophene, 2,3-trimethylenethiophene, 2,3-tetramethylenefurane, 3,4-tetramethylenepyridine or

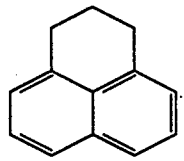

Owing to their good activity as herbicide antagonists, special mention should be made of those compounds wherein either a) R$_b$ is hydrogen, or b) the sulfamoyl group occupies the 4-position of the phenyl ring, or c) R$_2$ and R$_3$ are hydrogen, or d) A is the group

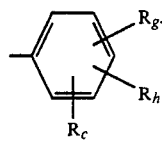

A preferred group of compounds of formula I comprises those compounds wherein R$_b$ is hydrogen and the sulfamoyl group occupies the 4-position of the phenyl ring. Also preferred are those compounds wherein R$_2$, R$_3$ and R$_6$ are hydrogen and the sulfamoyl group occupies the 4-position of the phenyl ring.

Furthermore, of the compounds of sub-group d), preferred compounds are those wherein R$_2$, R$_3$ and R$_b$ are hydrogen and the sulfamoyl group occupies the 4-position of the phenyl ring.

Of the compounds according to the invention, those falling within the scope of sub-formula Ia

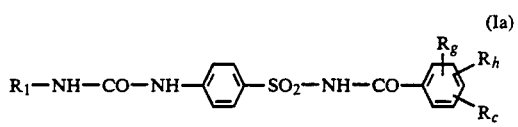

(Ia)

wherein R$_1$, R$_c$, R$_g$ and R$_h$ are as defined under formula I, are worthy of very special interest.

The compounds of formula Ia wherein R$_c$ is hydrogen are further preferred in respect of their action. A further sub-group worthy of special mention comprises the compounds of formula Ia wherein the radicals R$_1$, R$_g$ and R$_h$ are C$_1$-C$_4$alkyl groups.

The following individual compounds according to the invention falling within the scope of formula I are preferred:

1-[4-(N-4-methylbenzoylsulfamoyl)-phenyl]-3-methylurea, 1-[4-(N-3-methylbenzoylsulfamoyl)- phenyl]-3-methylurea, 1-[4-(N-4-tert.-butylbenzoylsulfamoyl)-phenyl]-3-methylurea, 1-[4-(N-3-trifluoromethylbenzoylsulfamoyl)-phenyl]-3-methylurea, 1-[4-(N-4-nitrobenzoylsulfamoyl)-phenyl]-3-methylurea, 1-[4-(N-2,3-dimethylbenzoylsulfamoyl)-phenyl]-3-methylurea, 1-[4-(N-3,4-dimethylbenzoylsulfamoyl)-phenyl]-3-methylurea, 1-[4-(N-3,4-dimethylbenzoylsulfamoyl)-phenyl]-3,3-dimethylurea, 1-[4-(N-3,4-dimethylbenzoylsulfamoyl)-phenyl]-3-ethylurea, 1-[4-(N-3,4-dimethylbenzoylsulfamoyl)-phenyl]-3-allylurea, 1-[4-(N-3,4-dimethylbenzoyl-sulfamoyl)-phenyl]-3-phenylurea, 1-[4-(N-3,5-dimethylbenzoylsulfamoyl)-phenyl]-3-methylurea, 1-[4-(N-3,4-dichlorobenzoylsulfamoyl)-phenyl]-3-methylurea, 1-[4-(N-3,4-dimethoxybenzoylsulfamoyl)-phenyl]-3-methylurea, 1-[4-(N-3,4-dimethoxybenzoylsulfamoyl)-phenyl]-3,3-dimethylurea, 1-[4-(N-2,4,5-trimethoxybenzoylsulfamoyl)-phenyl]-3-methylurea, 1-[4-(N-1-naphthylcarbonylsulfamoyl)-phenyl]-3-methylurea, 1-[4-(N-2-furylcarbonylsulfamoyl)-phenyl]-3-methylurea, 1-[4-(N-2-furylcarbonylsulfamoyl)-phenyl]-3,3-dimethylurea, 1-[4-(N-2-thienylcarbonylsulfamoyl)-phenyl]-3-methylurea, 1-[4-(N-piperonyloylsulfamoyl)-phenyl]-3-methylurea, 1-[4-(N-3-methylbenzoylsulfamoyl)-phenyl]-3,3-dimethylurea, 1-[4-(N-3-trifluoromethylbenzoylsulfamoyl)-phenyl]-3-cyclopropylurea, 1-[3-(N-3,4-dimethylbenzoylsulfamoyl)-phenyl]-3-methylurea, and 1-[3-(N-2-furylcarbonylsulfamoyl)-phenyl]-3,3-dimethylurea.

The compounds of formula I wherein $R_1$ is as defined under formula I with the exception of hydrogen and $R_2$ is hydrogen, are prepared by reacting a sulfamoylaniline of formula V

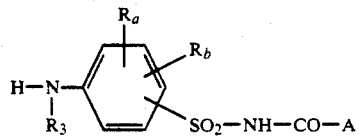

wherein A, $R_3$, $R_a$ and $R_b$ are as defined under formula I, with an isocyanate of formula VI $$R_1-N=C=O \quad (VI)$$

wherein $R_1$ is as defined under formula I with the exception of hydrogen.

By reaction with alkylating reagents of formula $$Lg-R_2$$

wherein Lg is a leaving group such as halogen, tosyl, $C_6H_5-SO_3-$ or $CH_3OSO_3-$ and $R_2$ is as defined under formula I with the exception of hydrogen, it is possible to prepare those compounds of formula I wherein $R_2$ is other than hydrogen. The reaction of the aniline derivatives of formula V with the isocyanate of formula VI can be carried out either without a solvent or in the presence of an aprotic inert organic solvent. The reactions are advantageously carried out in a solvent. Suitable solvents are hydrocarbons such as benzene, toluene, xylene or cyclohexane, carbon tetrachloride or chlorobenzene, ethers such as diethyl ether, ethylene glycol dimethyl ether, diethylene glycol dimethyl ether, tetrahydrofuran or dioxane, nitriles such as acetonitrile or propionitrile, amides such as dimethylformamide, diethylformamide or N-methylpyrrolidinone. The reaction temperatures are preferably from −20° to +120° C. The reactions occurring in the coupling processes are generally slightly exothermic and can be carried out at room temperature. In order to reduce the reaction time or also to initiate the reaction, it is expedient to heat the reaction mixture for a short time up to boiling point. The reaction times can also be reduced by the addition of a few drops of base as catalyst. Suitable bases are especially tertiary amines such as trimethylamine, triethylamine, quinuclidine, N,N-dimethylaminopyridine, pyridine, 1,4-diazabicyclo[2.2.2]octane, 1,5-diazabicyclo[4.3.0]non-5-ene or 1,8-diazabicyclo[5.4.0]undec-7-ene. The end products of formula I can either be isolated directly as a crystallisate or by concentration and/or evaporation of the solvent and purified by recrystallisation or trituration of the solid residue in solvents in which they are not readily soluble.

In accordance with a second process, the compounds of formula I are obtained by acylating a sulfamoylphenylurea of formula VII

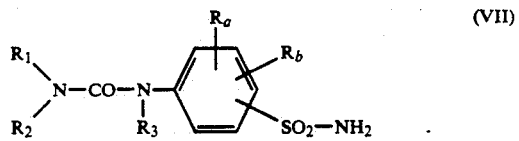

wherein $R_1$, $R_2$, $R_3$, $R_a$ and $R_b$ are as defined under formula I, with a carboxylic acid halide of formula VIII $$Hal-CO-A \quad (VIII)$$

wherein A is as defined under formula I and Hal is chlorine or bromine.

The reaction of the sulfamoylphenylurea of formula VII with the acylating reagent of formula VIII is advantageously carried out in the presence of an acid-binding agent in an inert organic solvent. Suitable solvents are hydrocarbons such as benzene, toluene, xylene or cyclohexane, carbon tetrachloride or chlorobenzene, ethers such as diethyl ether, ethylene glycol dimethyl ether, diethylene glycol dimethyl ether, tetrahydrofuran or dioxane, nitriles such as acetonitrile or propionitrile, amides such as dimethylformamide, diethylformamide or N-methylpyrrolidinone. The reaction temperatures are preferably from −20° to +120° C. The reactions occurring in the coupling processes are generally slightly exothermic and can be carried out at room temperature. In order to reduce the reaction time or also to initiate the reaction, it is expedient to heat the reaction mixture for a short time up to boiling point. The reaction times can also be reduced by the addition of a few drops of base as catalyst. Suitable bases are especially tertiary amines such as trimethylamine, triethylamine, quinuclidine, N,N-dimethylaminopyridine, pyridine, 1,4-diazabicyclo[2.2.2]octane, 1,5-diazabicyclo[4.3.0]non-5-ene or 1,8-diazabicyclo[5.4.0]undec-7-ene. It is also possible, however, to use as bases inorganic bases such as hydrides, such as sodium and calcium hydride, hydroxides such as sodium and potassium hydroxide, carbonates such as sodium and potassium carbonate or hydrogen carbonates such as potassium and sodium hydrogen carbonate. These bases can be used simultaneously as acid-binding agents. The end products of formula I can either be isolated directly as a crystallisate or by concentration and/or evaporation of the solvent and purified by recrystallisation or trituration of the solid residue in solvents in which they are not readily soluble.

The starting compounds of formulae V, VI, VII and VIII are generally known. Some of the compounds of formulae VI and VII are commercially available. Compounds of formulae V and VIII, for which no specific preparation processes have as yet been described in the literature, can be prepared in accordance with the following reaction schemes under the conditions customary for the individual reaction steps:

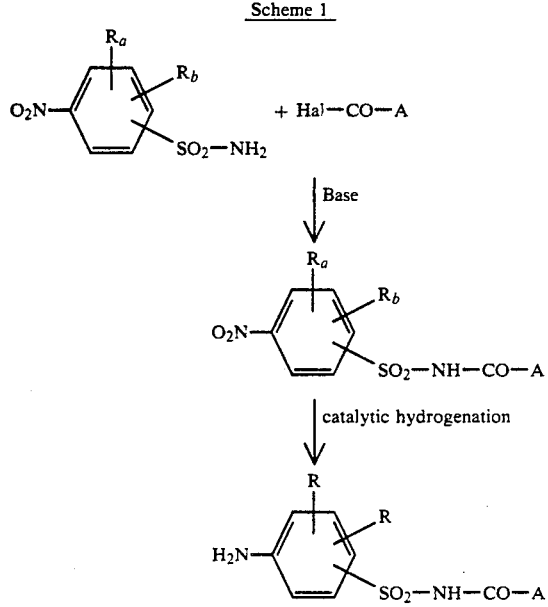

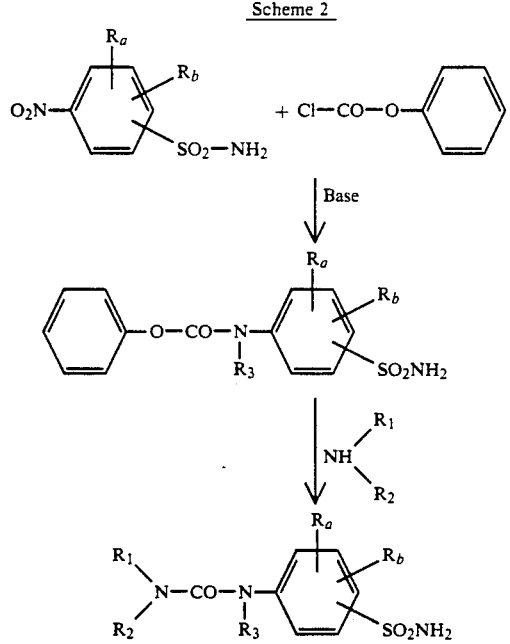

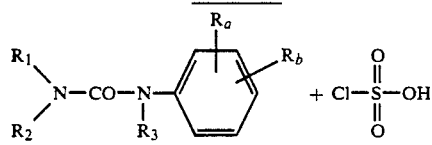

-continued
Scheme 3

The compounds of formula I are stable substances under normal laboratory conditions. They do not decompose when stored at room temperature.

A counter-agent or antidote of formula I can be used, according to the purpose of use, for pre-treating seeds of the cultivated plant (dressing of seeds or cuttings) or for application to the soil before or after sowing. It may, however, be applied on its own or together with the herbicide, before or after emergence of the plants. Treatment of the plants or the seed with the antidote can therefore be carried out in principle independently of the time of application of the herbicide. Treatment of the plants may, however, also be carried out by simultaneous application of the herbicide and the counter-agent (tank mix). Preemergence treatment includes both treatment of the cultivation area before sowing (ppi=-pre plant incorporation) and treatment of the sown cultivation area before emergence of the crop.

The amount of counter-agent applied in relation to the herbicide depends to a large extent on the mode of application. In the case of field treatment in which the herbicide and the counter-agent are applied either simultaneously (tank mix) or separately, the ratio of the amounts of counter-agent to herbicide is in the range of from 1:100 to 5:1. As a rule, full protective action is achieved with a ratio of counter-agent to herbicide of from 5:1 to 1:50. With seed dressing and similar selective protective measures, however, far smaller quantities of counter-agent are required in relation to the quantities of herbicide subsequently applied per hectare of cultivation area. In general, in the case of seed dressing, from 0.1 to 10 g of counter-agent are required per kg of seed. As a rule, full protective action is achieved with from 0.1 to 5 kg of counter-agent per kg of seed. If the counter-agent is to be applied by soaking the seed shortly before sowing, it is advantageous to use solutions of the counter-agent that contain the active ingredient in a concentration of from 1 to 10,000 ppm. As a rule, full protective action is achieved with counter-agent concentrations of from 100 to 1,000 ppm.

As a rule, there is a relatively long time lapse between protective measures, such as seed dressing and treatment of cuttings with a counteragent of formula I, and the possible later field treatment with herbicides. In agriculture, horticulture and forestry, pre-treated seeds and plant material may subsequently come into contact with a variety of chemicals. The invention therefore relates also to protective compositions for cultivated plants that contain, as active ingredient, a counter-agent of formula I together with customary carriers. Such compositions may optionally contain, in addition, those herbicides from whose effects the cultivated plants are to be protected. The invention relates also to propagation material from cultivated plants, such as seeds, plantlets and cuttings, that has been pretreated with compounds of formula I. The compounds of formula I are especially suitable for the treatment of seeds of cereals, soybeans and preferably sorghum, maize and rice.

Cultivated plants within the scope of the present invention are, for example, all types of cereal, such as wheat, rye, barley and oats, and also, especially, rice, cultivated sorghum, maize and soybeans. The compounds of formula I are preferably used to protect sorghum, maize and rice against the action of acylcyclohexanedione herbicides, sulfonylurea herbicides, chloroacetanilide herbicides or aryloxyphenoxypropionic acid herbicides.

Outstanding protective action against acylcyclohexanedione herbicides, sulfonylurea herbicides, aryloxyphenoxypropionic acid herbicides and chloroacetanilide herbicides is to be observed when the antidotes of formula I are used in maize, sorghum and rice. In particular, special mention should be made of the advantageous effect of the compound 1-[4-(N-3,4-dimethylbenzoylsulfamoyl)-phenyl]-3-methylurea.

Sulfonylurea herbicides, whose damaging effect on cultivated plants can be eliminated with the aid of the N-acylsulfamoylphenylureas of formula I, have recently become known in great number. Of the many publications devoted to the disclosure of herbicidally active sulfonylurea derivatives there may be mentioned by way of example U.S. Pat. No. 4,127,405 and published European Patent Applications EP-A-7687, EP-A-30142, EP-A-44807, EP-A-44808, EP-A-51466, EP-A-70802, EP-A-84020, EP-A-87780, EP-A-102925, EP-A-108708, EP-A-120814, EP-A-136061, EP-A-184385, EP-A-206995 and EP-A-237292.

Typical examples of herbicidal sulfonylurea derivatives are encompassed by formula II

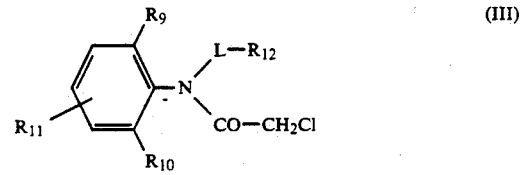

wherein E is a group

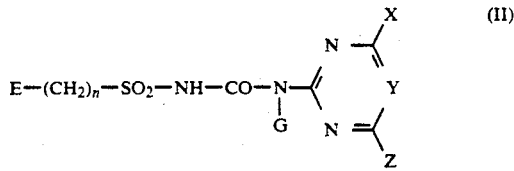

n is 0 or 1, G is hydrogen or methyl, X is methoxy, ethoxy, difluoromethoxy, methyl or chlorine, Y is CH or N, Z is methoxy, methyl, difluoromethoxy, cyclopropyl or methylamino, $R_4$ is $C_2$–$C_5$alkoxyalkoxy, $C_1$–$C_4$haloalkoxy, $C_1$–$C_4$haloalkylthio, $C_2$–$C_4$haloalkenyl, chlorine or $C_1$–$C_4$alkoxycarbonyl, $R_5$ is trifluoromethyl or di($C_1$–$C_4$alkyl)carbamoyl, $R_6$ is $C_1$–$C_4$alkoxycarbonyl, $R_7$ is $C_1$–$C_4$alkoxycarbonyl, and $R_8$ is $C_1$–$C_4$alkyl.

The following individual herbicidally active substances fall within the scope of formula II: N-(3-trifluoromethylpyridin-2-ylsulfonyl)-N'-(4,6-dimethoxypyrimidin-2-yl)-urea, N-(3-dimethylcarbamoylpyridin-2-ylsulfonyl)-N'-(4,6-dimethoxy-pyrimidin-2-yl)-urea, N-(1-methyl-4-ethoxycarbonylpyrazol-2-ylsulfonyl)-N'-(4,6-dimethoxypyrimidin-2-yl)-urea, N-(2-methoxycarbonylthien-3-yl-sulfonyl)-N'-(4-methoxy-6-methyl-1,3,5-triazin-2-yl)-urea, N-(2-methoxy-carbonylbenzylsulfonyl)-N'-(4,6-dimethoxypyrimidin-2-yl)-urea, N-(2-methoxycarbonylphenylsulfonyl)-N'-(4,6-bis-difluoromethoxypyrimidin-2-yl)-urea, N-(2-methoxycarbonylphenylsulfonyl)-N'-(4-ethoxy-6-methylamino-1,3,5-triazin-2-yl)-urea, N-(2-methoxycarbonylphenylsulfonyl)-N'-(4-methoxy-6-methyl-1,3,5-triazin-2-yl)-urea, N-(2-ethoxycarbonylphenyl-sulfonyl)-N'-(4-chloro-6-methoxypyrimidin-2-yl)-urea, N-(2-methoxycarbonylphenylsulfonyl)-N'-(4-methoxy-6-methyl-1,3,5-triazin-2-yl)-N'-methylurea, N-(2-methoxycarbonylphenylsulfonyl)-N'-(4,6-dimethoxy-pyrimidin-2-yl)-urea, N-(2-chlorophenylsulfonyl)-N'-(4-methoxy-6-methyl-1,3,5-triazin-2-yl)-urea, N-[2-(2-chloroethoxy)-phenylsulfonyl]-N'-(4-methoxy-6-methyl-1,3,5-triazin-2-yl)-urea and N-[2-(2-methoxyethoxy)-phenylsulfonyl]-N'-(4,6-dimethoxy-1,3,5-triazin-2-yl)-urea.

Haloacetanilides, whose damaging effect on cultivated plants can be eliminated with the aid of the N-acylsulfamoylphenylureas of formula I, are already known in great number. Such haloacetanilides can be described by the following general formula III:

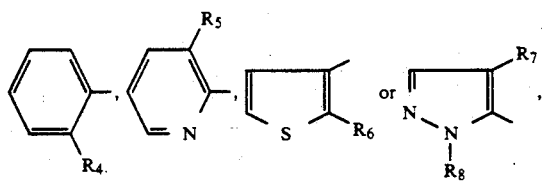

wherein L is a $C_1$–$C_4$alkylene bridge, each of $R_9$, $R_{10}$ and $R_{11}$, independently of the others, is hydrogen, halogen, $C_1$–$C_4$alkyl, $C_1$–$C_4$alkoxy, $C_1$–$C_4$haloalkyl, $C_2$–$C_5$alkoxyalkyl or $C_2$–$C_5$alkylthioalkyl, and $R_{12}$ is $C_1$–$C_4$alkoxy, —COOH, $C_1$–$C_4$alkoxycarbonyl, —CONH$_2$, $C_1$–$C_4$alkylcarbamoyl, di-$C_1$–$C_4$alkylcarbamoyl, cyano, $C_1$–$C_4$alkylcarbonyl, unsubstituted or substituted benzoyl, unsubstituted or substituted furyl, unsubstituted or substituted thienyl, unsubstituted or substituted pyrrolyl, unsubstituted or substituted pyrazolyl, unsubstituted or substituted 1,3,4-oxadiazol-2-yl, unsubstituted or substituted 1,3,4-thiadiazol-2-yl, unsubstituted or substituted 1,2,4-triazol-3-yl, unsubstituted or substituted dioxolanyl, unsubstituted or substituted dioxanyl, unsubstituted or substituted 1,3,4-triazol-2-yl or unsubstituted or substituted tetrahydrofuryl.

The following herbicidal chloroacetanilide derivatives especially fall within the scope of formula III:
N-ethoxymethyl-N-chloroacetyl-2-ethyl-6-methylaniline, N-chloroacetyl-N-methoxymethyl-2,6-diethylaniline, N-chloroacetyl-N-(2-methoxyethyl)-2,6-dimethylaniline, N-chloroacetyl-N-(2-n-propoxyethyl)-2,6-dimethylaniline, N-chloroacetyl-N-(2-isopropoxyethyl)-2,6-dimethylaniline, N-chloroacetyl-N-(2-methoxyethyl)-2-ethyl-6-methylaniline, N-chloroacetyl-N-(methoxyethyl)-2,6-diethylaniline, N-(2-ethoxyethyl)-N-chloroacetyl-2-ethyl-6-methylaniline, N-chloroacetyl- N-(2-methoxy-1-methylethyl)-2-methylaniline, N-chloroacetyl-N-(2-methoxy-1-methylethyl)-2,6-dimethylaniline, N-chloroacetyl-N-(2-methoxy-1-methylethyl)-2,6-diethylaniline, N-chloroacetyl-N-(2-methoxy-1-methylethyl))-2-ethyl-6-methylaniline, N-(2-ethoxyethyl)-N-chloroacetyl-2,6-diethylaniline, N-chloroacetyl-N-(2-n-propoxyethyl)-2-ethyl-6-methylaniline, N-chloroacetyl-N-(2-n-propoxyethyl)-2,6-diethylaniline, N-chloroacetyl-N-(2-isopropoxyethyl)-2-ethyl-6-methylaniline, N-ethoxycarbonylmethyl-N-chloroacetyl-2,6-dimethylaniline, N-ethoxycarbonylmethyl-N-chloroacetyl-2,6-diethylaniline, N-chloroacetyl-N-methoxycarbonylmethyl-2,6-dimethylaniline, N-chloroacetyl-N-(2,2-diethoxyethyl)-2,6-dimethylaniline, N-chloroacetyl-N-(2-methoxy-1-methylethyl)-2,3-dimethylaniline, N-(2-ethoxyethyl)-N-chloroacetyl-2-methylaniline, N-chloroacetyl-N-(2-methoxyethyl)-2-methylaniline, N-chloroacetyl-N-(2-methoxy-2-methylethyl)-2,6-dimethylaniline, N-(2-ethoxy-2-methylethyl)-N-chloroacetyl-2-ethyl-6-methylaniline, N-chloroacetyl-N-(1-ethyl-1-methoxyethyl)-2,6-dimethylaniline, N-chloroacetyl-N-(2-methoxyethyl)-2-methoxy-6-methylaniline, N-n-butoxymethyl-N-chloroacetyl-2-tert.-butylaniline, N-(2-ethoxyethyl-2-methylethyl)-2,6-dimethylaniline, N-chloroacetyl-N-(2-methoxyethyl)-2-chloro-6-methylaniline, N-(2-ethoxyethyl)-N-chloroacetyl-2-chloro-6-methylaniline, N-(2-ethoxyethyl)-N-chloroacetyl-2,3,6-trimethylaniline, N-chloroacetyl-1-(2-methoxyethyl)-2,3,6-trimethylaniline, N-chloroacetyl-N-cyanomethyl-2,6-dimethylaniline, N-chloroacetyl-N-(1,3-dioxolan-2-ylmethyl)-2,6-dimethylaniline, N-chloroacetyl-N-(1,3-dioxolan-2-ylmethyl)-2-ethyl-6-methylaniline, N-chloroacetyl-N-(1,3-dioxan-2-ylmethyl)-2-ethyl-6-methylaniline, N-chloroacetyl-N-(2-furylmethyl)-2,6-dimethylaniline, N-chloroacetyl-N-(2-furylmethyl)-2-ethyl-6-methylaniline, N-chloroacetyl-N-(2-tetrahydrofurylmethyl)-2,6-dimethylaniline, N-chloroacetyl-N-(N,N-dimethylcarbamoylmethyl)-2,6-dimethylaniline, N-(n-butoxymethyl)-N-chloroacetyl-2,6-diethylaniline, N-(2-n-butoxyethyl)-N-chloroacetyl-2,6-diethylaniline, N-chloroacetyl-N-(2-methoxy-1,2-dimethylethyl)-2,6-dimethylaniline, N-chloroacetyl-N-isopropyl-2,3-dimethylaniline, N-chloroacetyl-N-isopropyl-2-chloroaniline, N-chloroacetyl-N-(1H-pyrazol-1-yl-methyl)-2,6-dimethylaniline, N-chloroacetyl-N-(1H-pyrazol-1-ylmethyl)-2-ethyl-6-methylaniline, N-chloroacetyl-N-(1H-1,2,4-triazol-1-ylmethyl)-2,6-dimethylaniline, N-chloroacetyl-N-(1H-1,2,4-triazol-1-ylmethyl)-2,6-diethylaniline, N-benzoylmethyl-N-chloroacetyl-2,6-diethylaniline, N-benzoylmethyl-N-chloroacetyl-2-ethyl-6-methylaniline, N-chloroacetyl-N-(5-methyl-1,3,4-oxadiazol-2-yl)-2,6-diethylaniline, N-chloroacetyl-N-(5-methyl-1,3,4-oxadiazol-2-yl)-2-ethyl-6-methylaniline, N-chloroacetyl-N-(5-methyl-1,3,4-oxadiazol-2-yl)-2-tert.-butylaniline, N-chloroacetyl-N-(4-chlorobenzoylmethyl)-2,6-dimethylaniline and N-chloroacetyl-N-(1-methyl-5-methylthio-1,3,4-triazol-2-ylmethyl)-2,6-diethylaniline.

Aryloxyphenoxypropionic acid herbicides, whose damaging effect on cultivated plants can be eliminated with the aid of the N-acylsulfamoylphenylureas of formula I, are known in great number. Such aryloxyphenoxypropionic acid derivatives can be described by the following general formula IV:

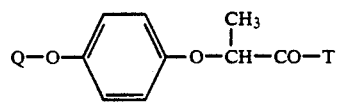

wherein Q is a radical

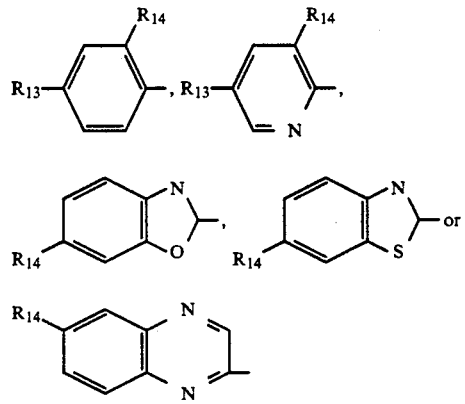

and T is $-NR_{15}R_{16}$, $-N(CN)R_{17}$, $-OR_{18}$, $SR_{18}$ or $-O-N=CR_{19}R_{20}$, wherein $R_{13}$ is halogen or trifluoromethyl, $R_{14}$ is hydrogen or halogen, each of $R_{15}$ and $R_{16}$, independently of the other, is hydrogen, $C_1-C_8$alkoxy, $C_1-C_8$alkyl, phenyl or benzyl, $R_{15}$ and $R_{16}$ together with the nitrogen atom carrying them form a 5- or 6-membered saturated nitrogen heterocycle that may be interrupted by an oxygen or a sulfur atom, $R_{17}$ is $C_1-C_4$alkyl, $C_3-C_4$alkenyl, $C_3-C_4$alkynyl or $C_2-C_4$alkoxyalkyl, $R_{18}$ is hydrogen or the equivalent of an alkali metal, alkaline earth metal, copper or iron ion; a quaternary $C_1-C_4$alkylammonium or $C_1-C_4$-hydroxyalkylammonium radical; a $C_1-C_9$alkyl radical that is unsubstituted or mono- or poly-substituted by amino, halogen, hydroxy, cyano, nitro, phenyl, $C_1-C_4$alkoxy, polyethoxy having from 2 to 6 ethylene oxide units, $-COOR_{21}$, $-COSR_{21}$, $-CONH_2$, $-CON(C_1-C_4$alkoxy$)-C_1-C_4$alkyl, $-CO-N-di-C_1-C_4$alkyl, $CONH-C_1-C_4$alkyl, $-N(C_1-C_4$alkoxy$)-C_1-C_4$alkyl or by di-$C_1-C_4$alkylamino; a $C_3-C_9$alkenyl radical that is unsubstituted or substituted by halogen or by $C_1-C_4$-alkoxy; a $C_3-C_9$alkynyl radical that is unsubstituted or substituted by halogen or by $C_1-C_4$alkoxy; $C_3-C_9$cycloalkyl; or phenyl that is unsubstituted or substituted by cyano, $C_1-C_4$alkyl, $C_1-C_4$alkoxy, acetyl, $-COOR_{21}$, $COSR_{21}$, $-CONH_2$, $-CON(C_1-C_4$alkoxy$)-C_1-C_4$alkyl, $-CO-N-di-C_1-C_4$alkyl or by $-CONH-C_1-C_4$alkyl, each of $R_{19}$ and $R_{20}$, independently of the other, is $C_1-C_4$alkyl, or together they form a 3- to 6-membered alkylene chain, and $R_{21}$ is hydrogen, $C_1-C_6$alkyl, $C_1-C_6$haloalkyl, $C_2-C_6$alkoxyalkyl, $C_3-C_6$alkenyl, $C_3-C_6$-haloalkyl, $C_3-C_6$alkynyl or $C_3-C_6$-haloalkynyl.

The following herbicidal aryloxyphenoxypropionic acid derivatives especially fall within the scope of formula IV:

2-[4-(5-chloro-3-fluoropyridin-2-yloxy)-phenoxy]-propionic acid propargyl ester,
2-[4-(3,5-dichloropyridin-2-yloxy)-phenoxy]-propionic acid propargyl ester,
2-[4-(3,5-dichloropyridin-2-yloxy)-phenoxy]-thiopropionic acid propargyl ester,
2-[4-(5-chloro-3-fluoropyridin-2-yloxy)-phenoxy]-propionic acid methyl ester, 2-[4-(5-chloro-3-fluoropyridin-2-yloxy)-phenoxy]-propionic acid butyl ester,
2-[4-(5-trifluoromethylpyridin-2-yloxy)-phenoxy]-propionic acid butyl ester,
2-[4-(5-trifluoromethylpyridin-2-yloxy)-phenoxy]-propionic acid methyl ester,
2-[4-(6-chloroquinoxalin-2-yloxy)-phenoxy]-propionic acid ethyl ester and
2-[4-(6-chlorobenzoxazolin-2-yloxy)-phenoxy]-propionic acid ethyl ester.

Acylcyclohexanedione derivatives, whose damaging effect on cultivated plants can be eliminated with the aid of the N-acylsulfamoylphenylureas of formula I, are described, for example, in published European Patent Application No. 0 243 313. Such acylcyclohexanedione derivatives can be described by the following general formula IX

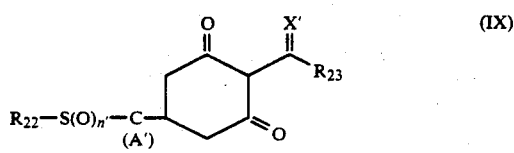

wherein A' is a 2- to 7-membered alkylene bridge, a 3- to 7-membered alkenylene bridge which can be mono- or poly-unsaturated, n' is 0, 1 or 2, $R_{22}$ is $C_1$-$C_4$alkyl or benzyl, $R_{23}$ is $C_1$-$C_6$alkyl unsubstituted or substituted by halogen, $C_1$-$C_4$alkoxy or by $C_1$-$C_4$alkylthio; $C_3$-$C_6$-cycloalkyl; phenyl, benzyl or phenylethyl wherein the phenyl ring can be substituted by halogen, $C_1$-$C_4$alkyl, $C_1$-$C_4$alkoxy, $C_1$-$C_4$alkylthio, $C_1$-$C_4$haloalkyl, $C_1$-$C_4$haloalkoxy, cyano or by nitro, X' is oxygen or a radical —$NOR_{24}$, and $R_{24}$ is $C_1$-$C_6$alkyl, $C_1$-$C_6$haloalkyl, $C_3$-$C_6$alkenyl, $C_3$-$C_6$haloalkenyl or $C_3$-$C_6$alkynyl.

The following herbicidal acylcyclohexanedione derivatives especially fall within the scope of formula IX:
5-(1-methylthiocyclobutan-1-yl)-2-(2,4-dichlorobenzoyl)-cyclohexane-1,3-dione,
5-(1-methylthiocyclobutan-1-yl)-2-n-butyrylcyclohexane-1,3-dione,
5-(1-methylthiocyclobutan-1-yl)-2-cyclopropylcarbonylcyclohexane-1,3-dione,
5-(1-methylthiocyclobutan-1-yl)-2-(2,3-dichlorobenzoyl)-cyclo-hexane-1,3-dione,
5-(1-methylsulfonylcyclobutan-1-yl)-2-n-butyrylcyclohexane-1,3-dione,
5-(1-methylthiocyclopropan-1-yl)-2-propionylcyclohexane-1,3-dione,
5-(1-ethylthiocyclopropan-1-yl)-2-propionylcyclo-hexane-1,3-dione and
5-(1-methylthiocyclopropan-1-yl)-2-n-butyrylcyclohexane-1,3-dione,
5-(1-methylthiocyclobutan-1-yl)-2-(1-ethoxyimino-n-butyryl)-cyclohexane-1,3-dione,
5-(1-methylthiocyclopropan-1-yl)-2-(1-ethoxyimino-n-butyryl)-cyclohexane-1,3-dione,
5-(1-methylthiocyclohexan-1-yl)-2-(1-ethoxyimino-n-butyryl)-cyclohexane-1,3-dione,
5-(1-methylthiocyclobutan-1-yl)-2-(1-allyloxyimino-n-butyryl)-cyclohexane-1,3-dione and
5-(1-methylthiocyclopentan-1-yl)-2-(1-ethoxyimino-n-butyryl)-cyclohexane-1,3-dione,
5-(1-methylthiocyclopropan-1-yl)-2-[1-(trans-3-chloroallyloxyimino)-n-butyryl]-cyclohexane-1,3-dione,
5-(1-methylthiocyclopropan-1-yl)-2-[1-(trans-3-chloroallyloxyimino)-propionyl]-cyclohexane-1,3-dione,
5-(1-methylthiocyclopropan-1-yl)-2-[1-(cis-3-chloroallyloxyimino)-propionyl]-cyclohexane-1,3-dione and
5-(1-ethylthiocyclopropan-1-yl)-2-[1-(trans-3-chloroallyloxyimino)-propionyl]-cyclohexane-1,3-dione.

The antidotes of formula I are most especially suitable for protecting cultivated plants from the herbicidal action of herbicides of formulae II, III and IV.

Agrochemical compositions that contain in a common formulation together with the antidote of formula I a sulfonylurea herbicide, a chloroacetanilide herbicide or an aryloxyphenoxypropionic acid herbicide are suitable for use as selective herbicides in crops of useful plants. The herbicidal compositions of the invention preferably contain, in addition to an antidote of formula I, a sulfonylurea of formula II, a chloroacetanilide of formula III, an acylcyclohexanedione derivative of formula IX or an aryloxyphenoxypropionic acid derivative of formula IV.

Unless used for dressing seed, the amount of counter-agent applied varies between about 0.01 and about 5 parts by weight per part by weight of herbicide. In practice, the most suitable ratio with regard to the optimum effect on the specific cultivated plant is determined from case to case, that is to say depending upon the type of herbicide used.

The invention relates also to a method of selectively controlling weeds in crops of cultivated plants, in which the crops of cultivated plants, parts of the cultivated plants or the cultivation areas of the cultivated plants are treated with a herbicide and a compound of formula I or with a composition containing that combination. The present invention relates also to the compositions containing the combination of herbicide and antidote.

The weeds to be controlled may be either monocotyledonous or dicotyledonous weeds.

Various methods and techniques are suitable for employing the compounds of formula I or compositions containing them for the protection of cultivated plants from the damaging effects of agrochemicals. Examples of these methods and techniques are:

i) Seed dressing
a) dressing the seed with an active ingredient formulated as a wettable powder, by shaking in a vessel until uniform distribution over the surface of the seed is achieved (dry dressing). In this procedure, about 10 to 500 g of active ingredient of formula I (40 g to 2 kg of wettable powder in the case of a 25% strength formulation) are used per 100 kg of seed.
b) dressing the seed with an emulsifiable concentrate of the active ingredient or with an aqueous solution of a wettable powder formulation of the active ingredient of formula I by method a) (wet dressing).
c) dressing by immersing the seed in a liquor containing from 50 to 3,200 ppm of an active ingredient of formula I for from 1 to 72 hours and, if desired, subsequently drying the seed (immersion dressing, seed soaking).

Dressing the seed or treating the sprouted seedling are, of course, the preferred methods of application since the treatment with the active ingredient is directed entirely towards the target crop. As a rule, from 10 g to 500 g, preferably from 50 to 400 g, of active ingredient are used per 100 kg of seed, and, depending upon the method employed, which also allows other active ingredients or micronutrients to be added, it is possible to exceed or use less than the concentration limits indicated (repeat dressing).

ii) Application from a tank mix

A liquid formulation of a mixture of counter-agent and herbicide (ratio of the one to the other from 10:1 to 1:30) is used, the application rate of herbicide being from 0.001 to 10 kg per hectare. A tank mix of this type is preferably applied before or after sowing or is worked 5 to 10 cm deep into the soil before sowing.

iii) Application to the seed furrow

The counter-agent is introduced in the form of an emulsifiable concentrate, wettable powder, or granulate into the open, sown seed furrow and then, after the seed furrow has been covered, the herbicide is applied in the normal manner according to the pre-emergence method.

iv) Controlled release of active ingredient

A solution of the active ingredient is adsorbed onto mineral granulate carriers or polymerised granules (urea/formaldehyde) and is allowed to dry. If desired, it is possible to apply a coating (coated granulate) which allows the active ingredient to be released in metered amounts over a specific period of time.

The compounds of formula I are used in unmodified form or, preferably, together with the adjuvants conventionally employed in the art of formulation and are therefore formulated e.g. into emulsifiable concentrates, directly sprayable or dilutable solutions, dilute emulsions, wettable powders, soluble powders, dusts, granulates, and also encapsulations. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonphenolpolyethoxyethanols, castor oil polyglycol ethers, polypropylene/polyethylene oxide adducts, tributylphenolpolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in the art of formulation are described inter alia in the following publications:

"1985 International McCutcheon's Emulsifiers & Detergents", Glen Rock NJ, USA, 1985, H. Stache, "Tensid-Taschenbuch", 2nd Edition, C. Hanser Verlag Munich, Vienna 1981, and M. and J. Ash, "Encyclopedia of Surfactants", Vol. I-III, Chemical Publishing Co., New York, 1980-1981.

The agrochemical compositions usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed especially of the following constituents (throughout percentages are by weight):

| Emulsifiable concentrates: | | |
|---|---|---|
| active ingredient mixture: | 1 to 20%, | preferably 5 to 10% |
| surfactant: | 5 to 30%, | preferably 10 to 20% |
| liquid carrier: | 50 to 94%, | preferably 70 to 85% |
| Dusts: | | |
| active ingredient mixture: | 0.1 to 10%, | preferably 0.1 to 1% |
| solid carrier: | 99.9 to 90%, | preferably 99.9 to 99% |
| Suspension concentrates: | | |
| active ingredient mixture: | 5 to 75%, | preferably 10 to 50% |
| water: | 94 to 25%, | preferably 88 to 30% |
| surfactant: | 1 to 40%, | preferably 2 to 30% |
| Wettable powders: | | |
| active ingredient mixture: | 0.5 to 90%, | preferably 1 to 80% |
| surfactant: | 0.5 to 20%, | preferably 1 to 15% |
| solid carrier: | 5 to 95%, | preferably 15 to 90% |
| Granulates: | | |
| active ingredient mixture: | 0.5 to 30%, | preferably 3 to 15% |
| solid carrier: | 99.5 to 70%, | preferably 97 to 85% |

Whereas commercial products will preferably be formulated as concentrates, the end user will normally employ dilute formulations. The formulations may be diluted down to a concentration of 0.001% active ingredient. The rates of application are normally from 0.01 to 10 kg a.i.(active ingredient)/ha, preferably from 0.25 to 5 kg a.i./ha.

The compositions may also contain further auxiliaries such as stabilisers, antifoams, preservatives, viscosity regulators, binders and tackifiers as well as fertilisers or other active ingredients for obtaining special effects.

The following Examples serve to illustrate the invention. They do not limit the invention.

PREPARATION EXAMPLES

Example P1

1-[4-(N-3,4-dimethylbenzoylsulfamoyl)-phenyl]-3-methylurea

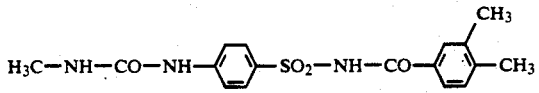

a) N-(4-sulfamoylphenyl)-O-phenylcarbamate.

176 g of sulfanilamide are suspended in 750 ml of dioxane, and 79 g of pyridine are added thereto. 160 g of chloroformic acid phenyl ester are then added dropwise to that mixture at 15° C. The reaction suspension is stirred at 50° C. for 1 hour, cooled and stirred into 2 liters of water. The precipitated product is separated off and dried, yielding 277 g of N-(4-sulfamoylphenyl)-O-phenylcarbamate, m.p. 220°-223° C.

b) 1-(4-sulfamoylphenyl)-3-methylurea.

330 ml of a 33% ethanolic methylamine solution are added dropwise at 80° C. to a suspension of 350 g of N-(4-sulfamoylphenyl)-O-phenylcarbamate in 1500 ml of ethanol. The product crystallises out of the initially clear solution within a period of 1.5 hours. After the reaction mixture has cooled, the precipitate is separated off and dried, yielding 256 g of 1-(4-sulfamoylphenyl)-3-methylurea, m.p. 211°-213° C.

c) 56.7 g of 3,4-dimethylbenzoyl chloride and 3.9 g of 4-dimethylaminopyridine are added to a suspension of 73.3 g of 1-(4-sulfamoylphenyl)-3-methylurea in 600 ml of acetonitrile. 98.1 g of triethylamine are added dropwise to that mixture, during which the temperature of the mixture rises from room temperature to 45° C. and the disperse constituents enter into solution. After a short time crystallisation begins. After a further 2.5 hours, the mixture is stirred into 2.5 liters of ice-water and 200 ml of 2N sulfuric acid. The precipitated product is separated off, washed with ether and dried, yielding 114.4 g of 1-[4-(N-3,4-dimethylbenzoylsulfamoyl)-phenyl]-3-methylurea, m.p. 236°-238° C. (with decomposition).

Example P2

1-[3-(N-2-furylcarbonylsulfamoyl)-phenyl]-3,3-dimethylurea

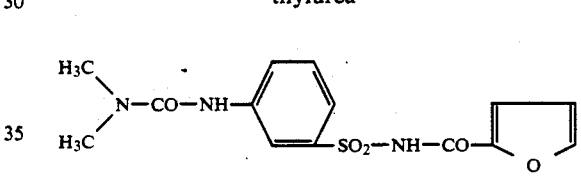

a) N-(3-sulfamoylphenyl)-O-phenylcarbamate.

113 g of chloroformic acid phenyl ester are added dropwise at 15° C. to a suspension of 125 g of 3-aminobenzenesulfonamide and 57.9 g of pyridine in 500 ml of dioxane. The mixture is stirred for one hour at room temperature and for one hour at 50° C. and then stirred into 2 liters of water. The precipitated product is separated off and dried, yielding 201 g of N-(3-sulfamoylphenyl)-O-phenylcarbamate, m.p. 184°-186° C. (with decomposition).

b) 1-(3-sulfamoylphenyl)-3,3-dimethylurea.

A mixture of 205 g of N-(3-sulfamoylphenyl)-O-phenylcarbamate and 158 g of a 40% aqueous solution of dimethylamine is heated at reflux in 500 ml of ethanol for 3 hours. The solvent is distilled off under reduced pressure. Water is added to the residue and the phenol that is formed is driven off with steam. After the distillation flask has cooled, the crystalline residue is separated off, washed with cold methanol and dried, yielding 136 g of 1-(3-sulfamoylphenyl)-3,3-dimethylurea, m.p. 193°-194° C.

c) 6.1 g of 2-furancarboxylic acid chloride and 0.1 g of 4-dimethylaminopyridine are added to a suspension of 10.1 g of 1-(3-sulfamoylphenyl)-3,3-dimethylurea in 60 ml of acetonitrile. 9.5 g of triethylamine are added dropwise to that mixture at room temperature. The reaction mixture is stirred for 15 hours at room temperature and for one hour at 60° C. After the mixture has cooled, 4.5 g of methanesulfonic acid are added dropwise thereto and the mixture is taken up in 1 liter of water. The oil that separates out crystallises after a short time. The crystals are separated off, washed with methanol and dried, yielding 11.3 g of 1-[3-(N-2-furylcarbonylsulfamoyl)-phenyl]-3,3-dimethylurea, m.p. 216°-217° C. (with decomposition).

Example P3

1-[4-(N-3,4-dimethylbenzoylsulfamoyl)-phenyl]-3-allylurea $$H_2C=CH-CH_2-NH-CO-NH-\underset{}{\bigcirc}-SO_2-NH-CO-\underset{CH_3}{\underset{|}{\bigcirc}}-CH_3$$

4.1 g of triethylamine are added dropwise to a suspension of 12.2 g of 4-(N-3,4-dimethylbenzoylsulfamoyl)-aniline in 20 ml of acetonitrile. Initially a clear solution is formed from which a salt precipitates. After the addition of 4.6 g of allyl isocyanate the mixture is stirred for 2 hours at room temperature and then for 2 hours at 70° C. When the mixture has cooled, it is taken up in a mixture of 1 liter of ice-water and 4.5 g of concentrated sulfuric acid. The resulting precipitate is separated off, washed with ether and dried, yielding 15.1 g of 1-[4-(N-3,4-dimethylbenzoylsulfamoyl)-phenyl]-3-allylurea, m.p. 194°-201° C. (with decomposition).

Example P4

1-[4-(N-2,3-dimethylbenzoylsulfamoyl)-phenyl]-3-methylurea

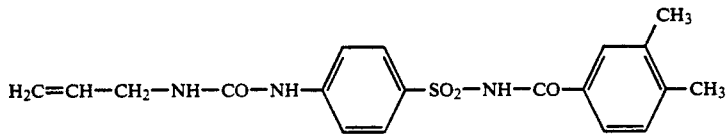

2.8 g of triethylamine are added to a suspension of 6.1 g of 4-(N-2,3-dimethylbenzoylsulfamoyl)-aniline in 50 ml of acetonitrile. 1.3 ml of methyl isocyanate are added dropwise to that mixture. The reaction mixture is stirred for 2 hours at room temperature and then for 6 hours at 50° C. After cooling to room temperature, the mixture is taken up in 200 ml of ice-water and 15 ml of 2N sulfuric acid. The precipitated product is separated off and dried, yielding 1-[4-(N-2,3-dimethylbenzoylsulfamoyl)-phenyl]-3-methylurea, m.p. 242°-244° C.

The intermediates and end products listed in the following Tables are obtained in analogous manner.

TABLE 1

$$\underset{R_2}{\overset{R_1}{>}}N-CO-NH-\underset{}{\bigcirc}-SO_2-NH-CO-A$$

| Comp. No. | $R_1R_2N-$ | A | m.p. [°C.] |
|---|---|---|---|
| 1.001 | Amino | Phenyl | |
| 1.002 | Methylamino | Phenyl | 237–238° (decomp.) |
| 1.003 | Dimethylamino | Phenyl | |
| 1.004 | Methylamino | 2-Tolyl | 234–236° (decomp.) |
| 1.005 | Methylamino | 3-Tolyl | 216–218° (decomp.) |
| 1.006 | Methylamino | 4-Tolyl | 247–249° (decomp.) |
| 1.007 | Methylamino | 4-Ethyl-phenyl | |
| 1.008 | Methylamino | 4-n-Propyl-phenyl | |
| 1.009 | Methylamino | 4-i-Propyl-phenyl | |
| 1.010 | Methylamino | 4-n-Butyl-phenyl | |
| 1.011 | Methylamino | 4-tert-Butyl-phenyl | 250–252° (decomp.) |
| 1.012 | Methylamino | 2-Chlorophenyl | 239–241° (decomp.) |
| 1.013 | Methylamino | 3-Chlorophenyl | 222–224° (decomp.) |
| 1.014 | Methylamino | 4-Chlorophenyl | 246–247° (decomp.) |
| 1.015 | Methylamino | 2-Fluorophenyl | 227–229° (decomp.) |
| 1.016 | Methylamino | 3-Fluorophenyl | 234–235° (decomp.) |
| 1.017 | Methylamino | 4-Fluorophenyl | |
| 1.018 | Methylamino | 2-Bromophenyl | 244–245° (decomp.) |
| 1.019 | Methylamino | 3-Bromophenyl | |
| 1.020 | Methylamino | 4-Bromophenyl | |
| 1.021 | Methylamino | 2-Iodophenyl | |
| 1.022 | Methylamino | 3-Iodophenyl | |
| 1.023 | Methylamino | 4-Iodophenyl | |
| 1.024 | Methylamino | 3-Chloromethyl-phenyl | |
| 1.025 | Methylamino | 2-Trifluoromethyl-phenyl | |
| 1.026 | Methylamino | 3-Trifluoromethyl-phenyl | 231–233° (decomp.) |
| 1.027 | Methylamino | 4-Trifluoromethyl-phenyl | |
| 1.028 | Methylamino | 2-Methoxy-phenyl | 197–198° (decomp.) |
| 1.029 | Methylamino | 3-Methoxy-phenyl | |
| 1.030 | Methylamino | 4-Methoxy-phenyl | |
| 1.031 | Methylamino | 2-Ethoxy-phenyl | 194–196° |
| 1.032 | Methylamino | 3-Ethoxy-phenyl | |
| 1.033 | Methylamino | 4-Ethoxy-phenyl | |
| 1.034 | Methylamino | 2-Methylmercapto-phenyl | |
| 1.035 | Methylamino | 2-Methylsulfonyl-phenyl | |
| 1.036 | Methylamino | 2-Methoxycarbonyl-phenyl | |
| 1.037 | Methylamino | 4-Methoxycarbonyl-phenyl | |

TABLE 1-continued $$R_1R_2N-CO-NH-C_6H_4-SO_2-NH-CO-A$$

| Comp. No. | R₁R₂N— | A | m.p. [°C.] |
|---|---|---|---|
| 1.038 | Methylamino | 2-Nitro-phenyl | |
| 1.039 | Methylamino | 3-Nitro-phenyl | |
| 1.040 | Methylamino | 4-Nitro-phenyl | 237–238° (decomp.) |
| 1.041 | Methylamino | 2-Acetyl-phenyl | |
| 1.042 | Methylamino | 4-Acetyl-phenyl | |
| 1.043 | Methylamino | 3-Cyanophenyl | |
| 1.044 | Methylamino | 4-Cyanophenyl | |
| 1.045 | Methylamino | 2,3-Dimethyl-phenyl | 242–244° (decomp.) |
| 1.046 | Methylamino | 2,4-Dimethyl-phenyl | 239–241° (decomp.) |
| 1.047 | Methylamino | 2,5-Dimethyl-phenyl | 223–224° (decomp.) |
| 1.048 | Methylamino | 2,6-Dimethyl-phenyl | |
| 1.049 | Amino | 3,4-Dimethyl-phenyl | 151–153° (decomp.) |
| 1.050 | Methylamino | 3,4-Dimethyl-phenyl | 236–238° (decomp.) |
| 1.051 | Dimethylamino | 3,4-Dimethyl-phenyl | 233–235° (decomp.) |
| 1.052 | Ethylamino | 3,4-Dimethyl-phenyl | >230° (decomp.) |
| 1.053 | Propylamino | 3,4-Dimethyl-phenyl | 211–213° (decomp.) |
| 1.054 | Isopropylamino | 3,4-Dimethyl-phenyl | 235–236° (decomp.) |
| 1.055 | Cyclopropylamino | 3,4-Dimethyl-phenyl | 229–231° (decomp.) |
| 1.056 | Butylamino | 3,4-Dimethyl-phenyl | 200–202° (decomp.) |
| 1.057 | Isobutylamino | 3,4-Dimethyl-phenyl | 222–223° (decomp.) |
| 1.058 | sec.-Butylamino | 3,4-Dimethyl-phenyl | 215–218° (decomp.) |
| 1.059 | tert.-Butylamino | 3,4-Dimethyl-phenyl | 223–225° (decomp.) |
| 1.060 | Allylamino | 3,4-Dimethyl-phenyl | 194–201° (decomp.) |
| 1.061 | Propyrgylamino | 3,4-Dimethyl-phenyl | 231–233° (decomp.) |
| 1.062 | Cyclohexylamino | 3,4-Dimethyl-phenyl | |
| 1.063 | Phenylamino | 3,4-Dimethyl-phenyl | 230–231° (decomp.) |
| 1.064 | 2-Methoxy-ethylamino | 3,4-Dimethyl-phenyl | 166–169° (decomp.) |
| 1.065 | Benzylamino | 3,4-Dimethyl-phenyl | 234–236° (decomp.) |
| 1.066 | Pyrrolidinyl | 3,4-Dimethyl-phenyl | |
| 1.067 | Piperidinyl | 3,4-Dimethyl-phenyl | |
| 1.068 | Hexahydroazepinyl | 3,4-Dimethyl-phenyl | 242–244° (decomp.) |
| 1.069 | Morpholinyl | 3,4-Dimethyl-phenyl | |
| 1.070 | 2-Methyl-piperidinyl | 3,4-Dimethyl-phenyl | |
| 1.071 | 3-Methyl-piperidinyl | 3,4-Dimethyl-phenyl | |
| 1.072 | 4-Methyl-piperidinyl | 3,4-Dimethyl-phenyl | |
| 1.073 | 2,6-Dimethyl-piperidinyl | 3,4-Dimethyl-phenyl | |
| 1.074 | N-Methyl-piperazinyl | 3,4-Dimethyl-phenyl | |
| 1.075 | Thiomorpholinyl | 3,4-Dimethyl-phenyl | |
| 1.076 | Methylamino | 3,5-Dimethyl-phenyl | 240–242° (decomp.) |
| 1.077 | Methylamino | 2,3-Dichlorophenyl | |
| 1.078 | Methylamino | 2,4-Dichlorophenyl | |
| 1.079 | Methylamino | 2,5-Dichlorophenyl | |
| 1.080 | Methylamino | 2,6-Dichlorophenyl | |
| 1.081 | Methylamino | 3,4-Dichlorophenyl | 240–241° (decomp.) |
| 1.082 | Methylamino | 3,5-Dichlorophenyl | |
| 1.083 | Methylamino | 2,3-Difluorophenyl | |
| 1.084 | Methylamino | 2,4-Difluorophenyl | |
| 1.085 | Methylamino | 2,5-Difluorophenyl | |
| 1.086 | Methylamino | 2,6-Difluorophenyl | |
| 1.087 | Methylamino | 3,4-Difluorophenyl | |
| 1.088 | Methylamino | 3,5-Difluorophenyl | |
| 1.089 | Methylamino | 3,5-Dimethoxy-phenyl | |
| 1.090 | Methylamino | 2,4-Dimethoxy-phenyl | |
| 1.091 | Methylamino | 2,5-Dimethoxy-phenyl | |
| 1.092 | Methylamino | 2,6-Dimethoxy-phenyl | |
| 1.093 | Methylamino | 3,4-Dimethoxy-phenyl | 223–225° (decomp.) |
| 1.094 | Dimethylamino | 3,4-Dimethoxy-phenyl | 203–207° (decomp.) |
| 1.095 | Methylamino | 3,5-Dimethoxy-phenyl | |
| 1.096 | Methylamino | 3,4-Dinitro-phenyl | |
| 1.097 | Methylamino | 3,5-Dinitro-phenyl | |
| 1.098 | Methylamino | 2-Chloro-3-nitro-phenyl | |
| 1.099 | Methylamino | 2-Chloro-4-nitro-phenyl | |
| 1.100 | Methylamino | 2-Chloro-5-nitro-phenyl | |
| 1.101 | Methylamino | 2-Chloro-2-nitro-phenyl | |
| 1.102 | Methylamino | 4-Chloro-2-nitro-phenyl | |
| 1.103 | Methylamino | 3-Chloro-3-nitro-phenyl | |
| 1.104 | Methylamino | 5-Chloro-2-nitro-phenyl | |
| 1.105 | Methylamino | 2-Methyl-3-nitro-phenyl | 247–248° (decomp.) |
| 1.106 | Methylamino | 2-Methyl-5-nitro-phenyl | |
| 1.107 | Methylamino | 2-Methyl-6-nitro-phenyl | |
| 1.108 | Methylamino | 3-Methyl-2-nitro-phenyl | |
| 1.109 | Methylamino | 3-Methyl-4-nitro-phenyl | |
| 1.110 | Methylamino | 4-Methyl-3-nitro-phenyl | |
| 1.111 | Methylamino | 5-Methyl-2-nitro-phenyl | |
| 1.112 | Methylamino | 4-Fluoro-3-nitro-phenyl | |

TABLE 1-continued $$R_1R_2N-CO-NH-\text{C}_6H_4-SO_2-NH-CO-A$$

| Comp. No. | R₁R₂N— | A | m.p. [°C.] |
|---|---|---|---|
| 1.113 | Methylamino | 5-Chloro-2-methoxy-phenyl | |
| 1.114 | Methylamino | 4-Chloro-2-methoxy-phenyl | |
| 1.115 | Methylamino | 4-Chloro-6-fluoro-phenyl | |
| 1.116 | Methylamino | 4-Chloro-2-fluoro-phenyl | |
| 1.117 | Methylamino | 2,4,6-Trimethyl-phenyl | |
| 1.118 | Methylamino | 2,4,5-Trimethoxy-phenyl | |
| 1.119 | Methylamino | 3,4,5-Trimethoxy-phenyl | 238–239° (decomp.) |
| 1.120 | Methylamino | 1-Naphthyl | 240–242° (decomp.) |
| 1.121 | Methylamino | 2-Naphthyl | 234–235° (decomp.) |
| 1.122 | Methylamino | 2-Furyl | 245–246° (decomp.) |
| 1.123 | Dimethylamino | 2-Furyl | 246–247° (decomp.) |
| 1.124 | Methylamino | 3-Furyl | (decomp.) |
| 1.125 | Methylamino | 2-Thienyl | 245–247° (decomp.) |
| 1.126 | Methylamino | 2-Chloropyridinyl | |
| 1.127 | Methylamino | 2,6-Dichloropyridinyl | 138–139° (decomp.) |
| 1.128 | Methylamino | 2,6-Dibromopyridinyl | |
| 1.129 | Methylamino | Piperonyl | 268–270° (decomp.) |
| 1.130 | Dimethylamino | 3-Tolyl | 204–207° (decomp.) |
| 1.131 | Cyclopropylamino | 3-Trifluoromethyl-phenyl | 246–247 (decomp.) |
| 1.132 | i-Propylamino | 3-Tolyl | 217–220° (decomp.) |
| 1.133 | Dimethylamino | 3-Trifluoromethylphenyl | 229–230° (decomp.) |
| 1.134 | Amino | 4-Chloro | 226–228° (decomp.) |
| 1.135 | Methylamino | 2-Carboxyphenyl | 181–183° (decomp.) |
| 1.136 | i-Propylamino | 2-Tolyl | 236–238° (decomp.) |
| 1.137 | Methylamino | 3-Bromo-4-Methylphenyl | 244–245° (decomp.) |
| 1.138 | i-Propylamino | 1-Naphthyl | |
| 1.139 | Allylamino | 1-Naphthyl | |
| 1.140 | Allylamino | 2-Tolyl | |
| 1.141 | 3-Tolylamino | 2-Tolyl | |
| 1.142 | tert.-Butylamino | 2-Tolyl | 144–145° (decomp.) |
| 1.143 | tert.-Butylamino | 2,4-Dimethylphenyl | 226–227° (decomp.) |
| 1.144 | Propargylamino | 1-Naphthyl | 149–151° (decomp.) |
| 1.145 | sec. Butylamino | 2,4-Dimethylphenyl | 230–232° (decomp.) |
| 1.146 | Propargylamino | 2,4-Dimethylphenyl | 191–192° (decomp.) |
| 1.147 | Methylamino | 2-Biphenyl | 262–264° (decomp.) |
| 1.148 | sec. Butylamino | 2,5-Dimethylphenyl | 208–210° (decomp.) |
| 1.149 | Dimethylamino | 2,4-Dimethylphenyl | 206–209° (decomp.) |
| 1.150 | Dimethylamino | 1-Naphthyl | >250° (decomp.) |
| 1.151 | Dimethylamino | 2-Tolyl | 236–240° (decomp.) |
| 1.152 | Propargylamino | 2,5-Dimethyl-phenyl | 198–200° (decomp.) |
| 1.153 | Methylamino | 4-Chloromethyl-phenyl | 228–229° (decomp.) |
| 1.154 | Methylamino | 3-(2,3-Tetramethylene)-thienyl | >250° |
| 1.155 | Methylamino | 3-(2,3-Tetramethylene)-furyl | |
| 1.156 | Methylamino | 3-(4,5-Dimethyl)-thienyl | 238–239° (decomp.) |
| 1.157 | Methylamino | 2-Propyloxy-phenyl | |
| 1.158 | Methylamino | 2-Butyloxy-phenyl | |
| 1.159 | Methylamino | 2-Isobutyloxy-phenyl | |
| 1.160 | Methylamino | 2-2'-Methoxyethoxy-phenyl | |
| 1.161 | Methylamino | 2-2'-Ethoxyethoxy-phenyl | |
| 1.162 | Methylamino | 2-2'-Fluoroethoxy-phenyl | |
| 1.163 | Methylamino | 2-2'-Chloroethoxy-phenyl | |
| 1.164 | Methylamino | 2-Allyloxy-phenyl | 201–204° |
| 1.165 | Methylamino | 2-2'-Methylallyloxy-phenyl | |
| 1.166 | Methylamino | 2-Crotyloxy-phenyl | |
| 1.167 | Methylamino | 2-2'-Chloroallyloxy-phenyl | |
| 1.168 | Methylamino | 2-3'-Chloroallyloxy-phenyl | |
| 1.169 | Methylamino | 2-Propargyloxy-phenyl | 189–191° |
| 1.170 | Dimethylamino | 2-Ethoxy-phenyl | |
| 1.171 | Dimethylamino | 2-Propyloxy-phenyl | |
| 1.172 | Dimethylamino | 2-Butyloxy-phenyl | |
| 1.173 | Dimethylamino | 2-Isobutyloxy-phenyl | |
| 1.174 | Dimethylamino | 2-2'-Methoxyethoxy-phenyl | |
| 1.175 | Dimethylamino | 2-2'-Ethoxyethoxy-phenyl | |
| 1.176 | Dimethylamino | 2-2'-Fluoroethoxy-phenyl | |
| 1.177 | Dimethylamino | 2-2'-Chloroethoxy-phenyl | |
| 1.178 | Dimethylamino | 2-Allyloxy-phenyl | |
| 1.179 | Dimethylamino | 2-2'-Methylallyloxy-phenyl | |
| 1.180 | Dimethylamino | 2-Crotyloxy-phenyl | |
| 1.181 | Dimethylamino | 2-2'-Chloroallyloxy-phenyl | |
| 1.182 | Dimethylamino | 2-3'-Chloroallyloxy-phenyl | |

TABLE 2

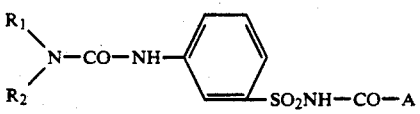

| Comp. No. | R₁R₂N— | A | m.p. [°C.] |
|---|---|---|---|
| 2.001 | Amino | Phenyl | |
| 2.002 | Methylamino | Phenyl | |
| 2.003 | Dimethylamino | Phenyl | |
| 2.004 | Methylamino | 2-Tolyl | |
| 2.005 | Methylamino | 3-Tolyl | |
| 2.006 | Methylamino | 4-Tolyl | |
| 2.007 | Methylamino | 2-Chlorophenyl | |
| 2.008 | Methylamino | 4-Chlorophenyl | |
| 2.009 | Methylamino | 3-Trifluoromethyl-phenyl | |
| 2.010 | Methylamino | 2,3-Dimethyl-phenyl | |
| 2.011 | Methylamino | 3,4-Dimethyl-phenyl | 147–152° |
| 2.012 | Methylamino | 1-Naphthyl | |
| 2.013 | Methylamino | 2-Naphthyl | |
| 2.014 | Dimethylamino | 2-Furyl | 216–217° (decomp.) |

TABLE 3

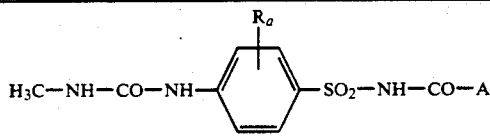

| Comp. No. | A | $R^a$ | m.p. [°C.] |
|---|---|---|---|
| 3.001 | Phenyl | 2-Fluoro | |
| 3.002 | Phenyl | 3-Fluoro | |
| 3.003 | 4-Tolyl | 2-Fluoro | 258–260° (decomp.) |
| 3.004 | 4-Tolyl | 3-Fluoro | ca. 270° (decomp.) |
| 3.005 | 4-Tolyl | 2-Chloro | |
| 3.006 | 4-Tolyl | 3-Chloro | |
| 3.007 | 4-Tolyl | 2-Methyl | |
| 3.008 | 4-Tolyl | 3-Methyl | |
| 3.009 | 3,4-Dimethyl-phenyl | 2-Fluoro | 246–248° (decomp.) |
| 3.010 | 3,4-Dimethyl-phenyl | 3-Fluoro | 239–240° |
| 3.011 | 3,4-Dimethyl-phenyl | 2-Chloro | |
| 3.012 | 3,4-Dimethyl-phenyl | 3-Chloro | 223–224° (decomp.) |
| 3.013 | 3,4-Dimethyl-phenyl | 2-Methyl | |
| 3.014 | 3,4-Dimethyl-phenyl | 3-Methyl | 218–220° (decomp.) |
| 3.015 | 2-Tolyl | 3-Fluoro | 236–238° (decomp.) |
| 3.016 | 1-Naphthyl | 3-Fluoro | 131–133° (decomp.) |
| 3.017 | 2,4-Dimethyl-phenyl | 2-Fluoro | 236–238° (decomp.) |
| 3.018 | 2,4-Dimethyl-phenyl | 3-Fluoro | 233–234° (decomp.) |
| 3.019 | 1-Naphthyl | 2-Fluoro | 240–241° (decomp.) |
| 3.020 | 2,3-Dimethyl-phenyl | 3-Fluoro | 227–230° (decomp.) |
| 3.021 | 2,3-Dimethyl-phenyl | 2-Fluoro | 244–246° (decomp.) |
| 3.022 | 2-Tolyl | 2-Fluoro | 236–237° (decomp.) |
| 3.023 | 3,5-Dimethyl-phenyl | 3-Fluoro | 198–200° (decomp.) |
| 3.024 | 3,5-Dimethyl-phenyl | 2-Fluoro | 244–246° (decomp.) |
| 3.025 | 2,5-Dimethyl-phenyl | 3-Fluoro | 213–215° (decomp.) |
| 3.026 | 2,5-Dimethyl-phenyl | 2-Fluoro | 227–229° (decomp.) |
| 3.027 | 2-Tolyl | 3-Methyl | 176° (decomp.) |
| 3.028 | 2-Tolyl | 3-Chloro | 218–220° (decomp.) |
| 3.029 | 1-Naphthyl | 3-Chloro | 150° (decomp.) |
| 3.030 | 1-Naphthyl | 3-Methyl | 153–155° (decomp.) |
| 3.031 | 2-Ethoxyphenyl | 2-Fluoro | |
| 3.032 | 2-Allylphenyl | 2-Fluoro | |
| 3.033 | 2-Propargylphenyl | 2-Fluoro | |
| 3.034 | 2-Ethoxyphenyl | 3-Fluoro | |
| 3.035 | 2-Allyloxyphenyl | 3-Fluoro | |
| 3.036 | 2-Propargylphenyl | 3-Fluoro | |
| 3.037 | 2-Ethoxyphenyl | 2-Methyl | |
| 3.038 | 2-Allyloxyphenyl | 2-Methyl | |
| 3.039 | 2-Propargylphenyl | 2-Methyl | |

TABLE 4

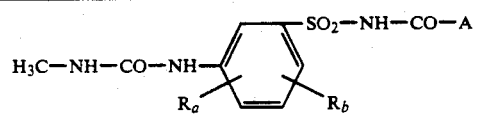

| Comp. No. | A | $R^a$ | $R^b$ | m.p. [°C.] |
|---|---|---|---|---|
| 4.001 | 1-Naphthyl | 2-Methyl | 6-Methyl | 214–216° (decomp.) |
| 4.002 | 3,4-Dimethyl-phenyl | 2-Methyl | 6-Methyl | 206–208° (decomp.) |
| 4.003 | 2-Tolyl | 2-Methyl | 6-Methyl | 217–219° (decomp.) |
| 4.004 | 1-Naphthyl | 2-Fluoro | 6-Fluoro | |
| 4.005 | 3,4-Dimethyl-phenyl | 2-Fluoro | 6-Fluoro | |
| 4.006 | 2-Tolyl | 2-Chloro | 6-Chloro | |
| 4.007 | 4-Tolyl | 2-Fluoro | 5-Fluoro | |
| 4.008 | 4-Tolyl | 2-Fluoro | 5-Fluoro | |
| 4.009 | 4-Tolyl | 2-Methyl | 5-Methyl | |

TABLE 5

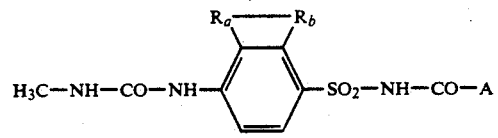

| Comp. No. | A | m.p. [°C.] |
|---|---|---|
| 5.001 | 3,4-Dimethyl-phenyl | 201–203° (decomp.) |

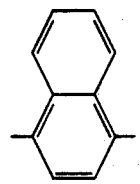

TABLE 5-continued

H₃C—NH—CO—NH—[benzene with Rₐ, Rᵦ]—SO₂—NH—CO—A

| Comp. No. | A | [Rₐ–Rᵦ ring system] | m.p. [°C.] |
|---|---|---|---|
| 5.002 | 2-Tolyl | naphthalene | 184–186° (decomp.) as triethylamine salt |
| 5.003 | 1-Naphthyl | naphthalene | 138–140° (decomp.) as triethylamine salt |
| 5.004 | 2-Tolyl | tetrahydronaphthalene | |
| 5.005 | 4-Tolyl | fluoro-tetrahydronaphthalene | |
| 5.006 | 3,4-Dimethyl-phenyl | indene | |
| 5.007 | 2-Tolyl | methyl-tetrahydronaphthalene | |

TABLE 6

(H₃C)(H₃CO)N—CO—NH—[phenyl]—SO₂—NH—CO—A

| Comp. No. | A | m.p. [°C.] |
|---|---|---|
| 6.001 | Phenyl | |
| 6.002 | 2-Tolyl | |
| 6.003 | 2,3-Dimethyl-phenyl | |
| 6.004 | 2,4-Dimethyl-phenyl | |
| 6.005 | 2,5-Dimethyl-phenyl | |
| 6.006 | 3,4-Dimethyl-phenyl | |
| 6.007 | 2-Methoxy-phenyl | 183–185° (decomp.) |
| 6.008 | 2-Ethoxy-phenyl | |
| 6.009 | 2,3-Dimethoxy-phenyl | |
| 6.010 | 2,4-Dimethoxy-phenyl | |
| 6.011 | 1-Naphthyl | 201–203° (decomp.) |
| 6.012 | 2-Naphthyl | |

FORMULATION EXAMPLES FOR ACTIVE INGREDIENTS OF FORMULA I OR MIXTURES THEREOF WITH HERBICIDES

| Example F1: Wettable powders | a) | b) | c) |
|---|---|---|---|
| compound 1.050 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| Example F2: Emulsifiable concentrate | a) | b) |
|---|---|---|
| compound 2.011 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any desired concentration can be produced from such concentrates by dilution with water.

| Example F3: Dusts | a) | b) |
|---|---|---|
| compound 1.050 | 0.1% | 1% |
| talcum | 99.9% | — |
| kaolin | — | 99% |

Ready-for-use dusts are obtained by mixing the active ingredient with the carrier and grinding the mixture in a suitable mill.

| Example F4: Extruder granulate | a) | b) |
|---|---|---|
| compound 1.006 | 10% | 1% |
| sodium lignosulfonate | 2% | 2% |
| carboxymethylcellulose | 1% | 1% |

| Example F4: Extruder granulate | a) | b) |
|---|---|---|
| kaolin | 87% | 96% |

The active ingredient is mixed and ground with the adjuvants, and the mixture is moistened with water. The mixture is extruded and then dried in a stream of air.

| Example F5: Coated granulate | |
|---|---|
| compound 1.005 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| Example F6: Suspension concentrate | a) | b) |
|---|---|---|
| compound 1.050 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

| Example F7: Salt solution | |
|---|---|
| compound 1.026 | 5% |
| isopropylamine | 1% |
| octylphenol polyethylene glycol ether (78 moles of ethylene oxide) | 3% |
| water | 91% |

| Example F8: Wettable powders | a) | b) | c) |
|---|---|---|---|
| compound 1.050 in admixture with N-[2-(2-methoxyethoxy)-phenylsulfonyl]-N'-(4,6-dimethoxy-1,3,5-triazin-2-yl]-urea sodium lignosulfonate | 20% | 60% | 0.5% |
|  | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient mixture is thoroughly mixed with the adjuvants and the resulting mixture is thoroughly ground in a suitable mill, affording wettable powders which can be diluted with water to give suspensions of the desired concentration.

| Example F9: Emulsifiable concentrate | a) | b) |
|---|---|---|
| compound 2.011 in admixture with 2-[4-(5-trifluoromethylpyridin-2-yloxy)-phenoxy]-propionic acid n-butyl ester octylphenol polyethylene glycol ether (4–5 moles of ethylene oxide) | 10% | 1% |
|  | 3% | 3% |
| calcium dodecylbenzenesulfonate | 3% | 3% |
| castor oil polyglycol ether (36 moles of ethylene oxide) | 4% | 4% |

| Example F9: Emulsifiable concentrate | a) | b) |
|---|---|---|
| cyclohexanone | 30% | 10% |
| xylene mixture | 50% | 79% |

Emulsions of any required concentration can be obtained from such concentrates by dilution with water.

| Example F10: Dusts | a) | b) |
|---|---|---|
| compound 1.050 in admixture with N-[2-(2-methoxyethoxy)-phenylsulfonyl]-N'-(4,6-dimethoxy-1,3,5-triazin-2-yl)-urea talcum | 0.1% | 1% |
|  | 99.9% | — |
| kaolin | — | 99% |

Ready-for-use dusts are obtained by mixing the active ingredient mixture with the carrier and grinding the resulting mixture in a suitable mill.

| Example F11: Extruder granulate: | a) | b) |
|---|---|---|
| compound 1.006 in admixture with N-[2-(2-methoxyethoxy)-phenylsulfonyl]-N'-(4,6-dimethoxy-1,3,5-triazin-2-yl)-urea sodium lignosulfonate | 10% | 1% |
|  | 2% | 2% |
| carboxymethylcellulose | 1% | 1% |
| kaolin | 87% | 96% |

The active ingredient mixture is mixed and ground with the adjuvants, and the resulting mixture is moistened with water. The mixture is extruded and then dried in a stream of air.

| Example F12: Coated granulate | |
|---|---|
| compound 1.005 in admixture with N-chloroacetyl-N-(2-methoxy-1-methylethyl)-2-ethyl-6-methylaniline polyethylene glycol (mol. wt. 200) | 3% |
|  | 3% |
| kaolin | 94% |

The finely ground active ingredient mixture is uniformly applied, in a mixer, to the kaolin moistened with polyethylene glycol. Non-dusty coated granulates are obtained in this manner.

| Example F13: Suspension concentrate | a) | b) |
|---|---|---|
| compound 1.050 in admixture with 2-[4-(6-chlorobenzoxazol-2-yloxy)-phenoxy]-propionic acid ethyl ester ethylene glycol | 40% | 5% |
|  | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

| Example F14: Salt solution | |
|---|---|
| compound 1.026 in admixture with 2-[4-(3,5-dichloropyridin-2-yloxy)-phenoxy]-propionic acid propargyl ester isopropylamine | 5% |
|  | 1% |
| octylphenol polyethylene glycol ether (78 moles of ethylene oxide) | 3% |
| water | 91% |

BIOLOGICAL EXAMPLES

The ability of the compounds of formula I to protect cultivated plants from the phytotoxic effect of potent herbicides can be seen from the following Examples. In the description of the tests, the compounds of formula I are referred to as antidotes (counter-agents or safeners).

The tests are evaluated firstly by determining the action of the herbicide alone as a percentage, 100% action corresponding to the death of the plants and 0% action denoting no action as in the untreated control plants. Secondly, the action of the herbicide/antidote combination is determined in the same manner also as the herbicidal action expressed as a percentage. The difference between the two resulting percentages is reproduced as "protective action in %" in the test results.

The action of the herbicide/antidote combination can be evaluated both in the case of direct simultaneous application of the two active ingredients as a tank mix in a single spraying operation and in the case of separate application, including application at different times, for example as in seed dressing with the antidote and post-emergence treatment with herbicide.

EXAMPLE B1

Test with herbicide and antidote in cultivated sorghum. Herbicide and antidote are applied together as a tank mix according to the pre-emergence or post-emergence method.

Sorghum seeds of the "Funk G-623" variety are sown in pots of 11 cm diameter filled with garden soil and are raised in a greenhouse under suitable temperature and light conditions. Water and fertiliser are supplied as required. In order to determine the pre-emergence action, a mixture of antidote and herbicide are applied in an amount of water of 550 l/ha immediately after sowing. In order to determine the post-emergence action, the active ingredient mixture is applied post-emergence when the plants are in the 3- to 5-leaf stage. In each case the test is evaluated 21 days after treatment to give the "protective action in percent".

Test results a) pre-emergence test:
test plant: sorghum "Funk G-623"
treatment: pre-emergence with a tank mix of 250 g/ha of compound 1.050 and 125 g/ha of N-[2-(2-methoxyethoxy)-phenylsulfonyl]-N'-(4,6-dimethoxy-1,3,5-triazin-2-yl)-urea. action: 21 days after application: 50% protective action.

b) post-emergence test:
test plant: sorghum "Funk G-623"
treatment: post-emergence with a tank mix of 250 g/ha of compound 1.050 and 125 g/ha of N-[2-(2-methoxyethoxy)-phenylsulfonyl]-N'-(4,6-dimethoxy-1,3,5-triazin-2-yl)-urea. action: 21 days after application: 45% protective action.

Example B2

Test with herbicide and antidote in maize and sorghum. The seeds are dressed with the antidote, the herbicide is applied according to the pre-emergence or post-emergence method.

Maize seeds of the "Blizzard" variety and sorghum seeds of the "Funk G-623" variety that have been dressed with the antidote are shown in pots of 11 cm diameter filled with garden soil and are raised in a greenhouse under suitable temperature and light conditions. Water and fertiliser are supplied as required. In order to determine the preemergence action, the herbicide is applied in an amount of water of 550 l/ha immediately after sowing. In order to determine the post-emergence action, the herbicide is applied post-emergence when the plants are in the 3- to 5-leaf stage. In each case the test is evaluated 12 to 26 days after treatment to give the "protective action in percent".

Test results a) Maize tests:
test plant: maize "Blizzard"
treatment: seed dressing with 0.5 g, 1 or 2 of compound 1.050 per kg of maize seed Herbicide pre-emergence 4000 g/ha of N-chloroacetyl-N-(2-methoxy-1-methoxyethyl)-ethyl-6-methylaniline, or 240 g/ha of N-[2-(3,3,3-trifluoropropen-1-yl)-phenylsulfonyl]-N'-(4-methoxy-6-methyl-1,3,5-triazin-2-yl)-urea, or 120, 60 or 30 g/ha of N-[2-(2-methoxyethoxy)-phenylsulfonyl]-N'-(4,6-dimethoxy-1,3,5-triazin-2-yl)-urea.

Herbicide post-emergence 120 g/ha of N-(2-methoxycarbonylthien-3-ylsulfonyl)-N'-(4-methoxy-6-methyl-1,3,5-triazin-2-yl)-urea, or 480 g/ha of N-[2-(3,3,3-trifluoropropen-1-yl)-phenylsulfonyl]-N'-(4-methoxy-6-methyl-1,3,5-triazin-2-yl)-urea, or 120 g/ha of N-(2-methoxycarbonylphenylsulfonyl)-N'-(4-difluoromethoxy-6-methoxypyrimidin-2-yl)-urea, or 120 g/ha of N-(2-methoxycarbonylphenylsulfonyl)-N'-(4-cyclopropyl-6-methoxy-1,3,5-triazin-2-yl)-urea, or 120 g/ha of N-(2-methoxycarbonylphenylsulfonyl)-N'-(4,6-bis-difluoromethoxypyrimidin-2-yl)-urea, or 10 g/ha of N-[2-(2-chloroethoxy)phenylsulfonyl]-N'-(4-methoxy-6-methyl-1,3,5-triazin-2-yl)-urea, or 30 g/ha of 2-[4-(6-chloroquinoxalin-2-yloxy)-phenoxy]-propionic acid ethyl ester, or 60 g/ha of 2-[4-(6-chlorobenzoxazol-2-yloxy)-phenoxy]-propionic acid ethyl ester, or 30 g/ha of 2-[4-(3,5-dichlorpyridin-2-yloxy)-phenoxy]-propionic acid propargyl ester, or 10 g/ha of N-(2-methoxycarbonylphenylsulfonyl)-N'-(4-ethoxy-6-methylamino-1,3,5-triazin-2-yl)-urea, or 240, 120, 60 or 30 g/ha of N-[2-(2-methoxyethoxy)-phenylsulfonyl]-N'-(4,6-dimethoxy-1,3,5-triazin-2-yl)-urea.

| Safener dressing quantity in g/kg seed | Herbicide-application rate in g/ha | Action: (DAT: days after treatment) | Mode of application of herbicide/evaluation | protective action in % |
|---|---|---|---|---|
| 2 | 4000 | N-Chloroacetyl-N-(2-methoxy-1-ethyl)-2-ethyl-6-methylaniline | pre/14 DAT | 40 |
| 1 | 240 | N-[2-(3,3,3-Trifluoropropen-1-yl)-phenylsulfonyl]-N'-(4-methoxy-6-methyl-1,3,5-triazin-2-yl)-urea | pre/20 DAT | 25 |

-continued

| Safener dressing quantity in g/kg seed | Herbicide-application rate in g/ha | | Mode of application of herbicide/evaluation | protective action in % |
|---|---|---|---|---|
| 1 | 480 | | post/20 DAT | 30 |
| 2 | 120 | N-[2-(2-Methoxyethoxy)-phenyl-sulfonyl]-N'-(4,6-dimethoxy-1,3,5-triazin-2-yl)-urea | pre/12 DAT | 70 |
| 1 | 120 | | pre/12 DAT | 65 |
| 0.5 | 120 | | pre/12 DAT | 65 |
| 2 | 60 | | pre/12 DAT | 65 |
| 1 | 60 | | pre/12 DAT | 65 |
| 0.5 | 60 | | pre/12 DAT | 70 |
| 2 | 30 | | pre/12 DAT | 55 |
| 1 | 30 | | pre/12 DAT | 50 |
| 0.5 | 30 | | pre/12 DAT | 55 |
| 2 | 240 | | post/20 DAT | 65 |
| 1 | 240 | | post/20 DAT | 65 |
| 0.5 | 240 | | post/20 DAT | 50 |
| 2 | 120 | | post/20 DAT | 60 |
| 1 | 120 | | post/20 DAT | 55 |
| 0.5 | 120 | | post/20 DAT | 25 |
| 2 | 60 | | post/20 DAT | 40 |
| 1 | 60 | | post/20 DAT | 40 |
| 0.5 | 60 | | post/20 DAT | 35 |
| 2 | 30 | | post/20 DAT | 25 |
| 1 | 30 | | post/20 DAT | 30 |
| 0.5 | 30 | | post/20 DAT | 15 |
| 1 | 120 | N-(2-Methoxycarbonylthien-3-yl-sulfonyl)-N'-(4-methoxy-6-methyl-1,3,5-triazin-2-yl)-urea | post/16 DAT | 20 |
| 1 | 120 | N-(2-Methoxycarbonylphenyl-sulfonyl-N'-(4-difluoromethoxy-6-methoxy-pyrimidin-2-yl)-urea | post/16 DAT | 15 |
| 1 | 120 | N-(2-Methoxycarbonylphenyl-sulfonyl-N'-(4-cyclopropyl-6-methoxy-1,3,5-triazin-2-yl)-urea | post/16 DAT | 20 |
| 1 | 120 | N-(2-Methoxycarbonylphenyl-sulfonyl-N'-(4,6-bis-difluoro-methoxy-pyrimidin-2-yl)-urea | post/16 DAT | 20 |
| 1 | 10 | N-[2-(2-Chloroethoxy)-phenyl-sulfonyl]-N'-(4-methoxy-6-methyl-1,3,5-triazin-2-yl)-urea | post/16 DAT | 35 |
| 1 | 30 | 2-[4-(6-Chloroquinoxalin-2-yloxy)-phenoxy]-propionic acid ethyl ester | post/16 DAT | 30 |
| 1 | 30 | 2-[4-(3,5-Dichloropyridin-2-yloxy)-phenoxy]-propionic acid propargyl ester | post/16 DAT | 45 |
| 1 | 10 | N-(2-Methoxycarbonylphenyl-sulfonyl)-N'-(4-ethoxy-6-methyl-amino-1,3,5-triazin-2-yl)-urea | post/16 DAT | 30 |
| 1 | 60 | 2-[4-(6-Chlorobenzoxazol-2-yloxy)-phenoxy]-propionic acid ethyl ester | post/16 DAT | 30 | b) Sorghum tests:
test plant: Sorghum "Funk G-623"
treatment: Seed dressing with 0.5 g, 1 or 2 g of compound 1.050 per kg of sorghum seed Herbicide pre-emergence 1000 g/ha of N-chloroacetyl-N-(2-methoxy-1-methoxyethyl)-ethyl-6-methylaniline, or 250 g/ha of N-[2-(3,3,3-trifluoropropen-1-yl)-phenylsulfonyl]-N'-(4-methoxy-6-methyl-1,3,5-triazin-2-yl)-urea, or 120, 60 or 30 g/ha of N-[2-(2-methoxyethoxy)-phenylsulfonyl]-N'-(4,6-dimethoxy-1,3,5-triazin-2-yl)-urea.

Herbicide post-emergence 480 g/ha of N-[2-(3,3,3-trifluoropropen-1-yl)-phenyl-sulfonyl]-N'-(4-methoxy-6-methyl-1,3,5-triazin-2-yl)urea, or 15 g/ha of 2-[4-(6-chloroquinoxalin-2-yloxy)-phenoxy]-propionic acid ethyl ester, or 60 g/ha of 2-[4-(6-chlorobenzoxazol-2-yloxy)-phenoxy]-propionic acid ethyl ester, or 15 g/ha of 2-[4-(3,5-dichloropyridin-2-yloxy)-phenoxy]-propionic acid propargyl ester, or 30 g/ha of 2-[4-(5-trifluoromethylpyridin-2-yloxy)-phenoxy]-propionic acid butyl ester, or 240, 120, 60 or 30 g/ha of N-[2-(2-methoxyethoxy)-phenylsulfonyl]-N'-(4,6-dimethoxy-1,3,5-triazin-2-yl)-urea.

| Safener dressing quantity in g/kg seed | Herbicide-application rate in g/ha | | Mode of application of herbicide/evaluation | protective action in % |
|---|---|---|---|---|
| 1 | 1000 | N-Chloroacetyl-N-(2-methoxy-1-ethyl)-2-ethyl-6-methylaniline | pre/26 DAT | 35 |
| 1 | 250 | N-[2-(3,3,3-Trifluoropropen-1-yl)- | pre/20 DAT | 45 |

| Safener dressing quantity in g/kg seed | Herbicide-application rate in g/ha | Action: (DAT: days after treatment) | Mode of application of herbicide/evaluation | protective action in % |
|---|---|---|---|---|
| | | phenylsulfonyl]-N'-(4-methoxy-6-methyl-1,3,5-triazin-2-yl)-urea | | |
| 1 | 480 | | post/20 DAT | 40 |
| 2 | 120 | N-[2-(2-Methoxyethoxy)-phenylsulfonyl]-N'-(4,6-dimethoxy-1,3,5-triazin-2-yl)-urea | pre/12 DAT | 55 |
| 1 | 120 | | pre/12 DAT | 55 |
| 0.5 | 120 | | pre/12 DAT | 60 |
| 2 | 60 | | pre/12 DAT | 55 |
| 1 | 60 | | pre/12 DAT | 50 |
| 0.5 | 60 | | pre/12 DAT | 60 |
| 2 | 30 | | pre/12 DAT | 70 |
| 1 | 30 | | pre/12 DAT | 65 |
| 0.5 | 30 | | pre/12 DAT | 70 |
| 2 | 240 | | post/20 DAT | 50 |
| 1 | 240 | | post/20 DAT | 60 |
| 0.5 | 240 | | post/20 DAT | 60 |
| 2 | 120 | | post/20 DAT | 50 |
| 1 | 120 | | post/20 DAT | 65 |
| 0.5 | 120 | | post/20 DAT | 60 |
| 2 | 60 | | post/20 DAT | 45 |
| 1 | 60 | | post/20 DAT | 65 |
| 0.5 | 60 | | post/20 DAT | 60 |
| 2 | 30 | | post/20 DAT | 30 |
| 1 | 30 | | post/20 DAT | 45 |
| 0.5 | 30 | | post/20 DAT | 50 |
| 1 | 60 | 2-[4-(6-Chlorobenzoxazol-2-yloxy)-phenoxy]-propionic acid ethyl ester | post/16 DAT | 33 |
| 1 | 15 | 2-[4-(6-Chloroquinoxalin-2-yloxy)-phenoxy]-propionic acid ethyl ester | post/16 DAT | 40 |
| 1 | 15 | 2-[4-(3,5-Dichloropyridin-2-yloxy)-phenoxy]-propionic acid propargyl ester | post/16 DAT | 50 |
| 1 | 30 | 2-[4-(5-Trifluoromethylpyridin-2-yloxy)-phenoxy]-propionic butyl ester | post/16 DAT | 20 |

Test results

Example B3

Test with herbicide and antidote in rice. The seeds are soaked in antidote dispersion, the herbicide is applied according to the pre-emergence method.

Rice seeds of the "S-201" variety are soaked for 48 hours in an aqueous dispersion of the antidote, then stored dry for 24 hours and finally sown on the surface in pots (9×9 cm) filled with boggy garden soil. Immediately after sowing the surface of the soil is sprayed with the herbicide in an amount of water of 550 l/ha. The plants are raised in a greenhouse under suitable temperature and light conditions. Water and fertiliser are supplied as required. The test is evaluated 26 days after treatment to give the "protective action in percent".

Test results test plant: rice "S-201"

treatment: 48 hours soaking of the seeds in a 300 ppm solution of compound 1.050 followed by pre-emergence application of 30 g/ha of N-[2-(2-methoxyethoxy)-phenylsulfonyl]-N'-(4,6-dimethoxy-1,3,5-triazin-2-yl)-urea action: 26 days after application: 55% protective action.

What is claimed is:

1. A N-acyl-sulfamoyl-phenyl urea compound of formula I

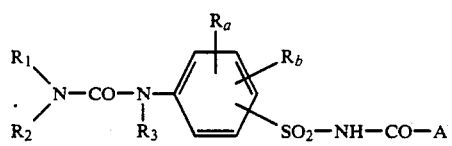

(I)

wherein

A is a radical selected from the group

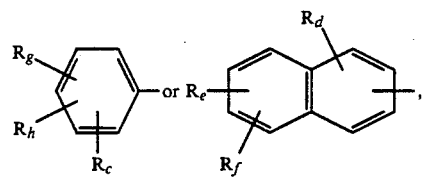

$R_1$ is $C_1$-$C_4$-alkoxy or each of $R_1$ and $R_2$, independently of the other, is hydrogen, $C_1$-$C_8$alkyl, $C_3$-$C_8$cycloalkyl, $C_3$-$C_6$alkenyl, $C_3$-$C_6$alkynyl,

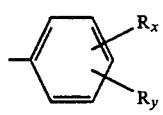

or $C_1$-$C_4$alkyl substituted by $C_1$-$C_4$alkoxy or by

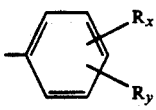

$R_3$ is hydrogen or $C_1$-$C_4$alkyl, $R_a$ is hydrogen, halogen, cyano, nitro, trifluoromethyl, $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, —COOR$_j$, —CONR$_k$R$_m$, —COR$_n$, —SO$_2$NR$_k$R$_m$ or —OSO$_2$—C$_1$-C$_4$alkyl, $R_g$ is hydrogen, halogen, cyano, nitro, $C_1$-$C_4$alkyl, $C_1$-$C_4$haloalkyl, $C_1$-$C_4$alkylthio, $C_1$-$C_4$alkylsulfinyl, $C_1$-$C_4$alkylsulfonyl, —COOR$_j$, —CONR$_k$R$_m$, —COR$_n$, —SO$_2$NR$_k$R$_m$ or —OSO$_2$—C$_1$-C$_4$alkyl, $C_1$-$C_6$alkoxy, $C_1$-$C_6$alkoxy substituted by $C_1$-$C_4$-alkoxy or halogen, $C_3$-$C_6$alkenyloxy, or $C_3$-$C_6$alkenyloxy substituted by halogen, or $C_3$-$C_6$-alkynyloxy, or $R_a$ and $R_b$ together form a $C_3$-$C_4$alkylene bridge, which can be substituted by halogen or by $C_1$-$C_4$alkyl, or a $C_3$-$C_4$alkenylene bridge, which can be substituted by halogen or by $C_1$-$C_4$alkyl, or a $C_4$alkadienylene bridge which can be substituted by halogen or by $C_1$-$C_4$alkyl, each of $R_b$ and $R_h$, independently of the other, is hydrogen, halogen, $C_1$-$C_4$alkyl, trifluoromethyl, $C_1$-$C_6$alkoxy, $C_1$-$C_6$alkylthio or —COOR$_j$, $R_c$ is hydrogen, halogen, nitro, $C_1$-$C_4$alkyl or methoxy, $R_d$ is hydrogen, halogen, nitro, $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, —COOR$_j$ or CONR$_k$R$_m$, $R_e$ is hydrogen, halogen, $C_1$-$C_4$alkyl, —COOR$_j$, trifluoromethyl or methoxy, or $R_d$ and $R_e$ together form a $C_3$-$C_4$alkylene bridge, $R_f$ is hydrogen, halogen or $C_1$-$C_4$alkyl, each of $R_x$ and $R_y$, independently of the other, is hydrogen, halogen, $C_1$-$C_4$alkyl, $C_1$-$C_4$alkoxy, $C_1$-$C_4$alkylthio, —COOR$_4$, trifluoromethyl, nitro or cyano, each of $R_j$, $R_k$ and $R_m$, independently of the others, is hydrogen or $C_1$-$C_4$alkyl.

2. A compound of formula I according to claim 1 wherein A is a radical selected from the group

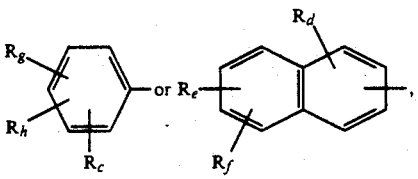

$R_1$ is $C_1$-$C_4$-alkoxy or
each of $R_1$ and $R_2$, independently of the other, is hydrogen, $C_1$-$C_8$alkyl, $C_3$-$C_8$cycloalkyl, $C_3$-$C_6$alkenyl, $C_3$-$C_6$alkynyl,

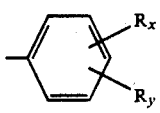

or $C_1$-$C_4$alkyl substituted by $C_1$-$C_4$alkoxy or by

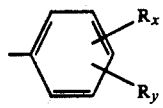

$R_3$ is hydrogen or $C_1$-$C_4$alkyl, $R_a$ is hydrogen, halogen, cyano, nitro, trifluoromethyl, $C_1$-$C_4$alkyl, $C_1$-$C_4$haloalkyl, $C_1$-$C_4$alkoxy, $C_1$-$C_4$alkylthio, $C_1$-$C_4$alkylsulfinyl, $C_1$-$C_4$alkylsulfonyl, —COOR$_j$, —CONR$_k$R$_m$, —COR$_n$, —SO$_2$NR$_k$R$_m$ or —OSO$_2$—C$_1$-C$_4$alkyl, $R_g$ is hydrogen, halogen, cyano, nitro, trifluoromethyl, $C_1$-$C_4$alkyl, $C_1$-$C_4$haloalkyl, $C_1$-$C_4$alkylthio, $C_1$-$C_4$alkylsulfinyl, $C_1$-$C_4$alkylsulfonyl, —COOR$_j$, —CONR$_k$R$_m$, —COR$_n$, —SO$_2$NR$_k$R$_m$ or —OSO$_2$—C$_1$-C$_4$alkyl, $C_1$-$C_6$alkoxy, $C_1$-$C_6$alkoxy substituted by $C_1$-$C_4$-alkoxy or halogen, $C_3$-$C_6$alkenyloxy, or $C_3$-$C_6$alkenyloxy substituted by halogen, or $C_3$-$C_6$-alkinyl, each of $R_b$ and $R_h$, independently of the other, is hydrogen, halogen, $C_1$-$C_4$alkyl, trifluoromethyl, methoxy, methylthio or —COOR$_j$, $R_c$ is hydrogen, halogen, nitro, $C_1$-$C_4$alkyl or methoxy, $R_d$ is hydrogen, halogen, nitro, $C_1$-$C_4$alkyl, $C_1$-$C_4$alkoxy, $C_1$-$C_4$alkylthio, $C_1$-$C_4$alkylsulfinyl, $C_1$-$C_4$alkylsulfonyl, —COOR$_j$ or CONR$_k$R$_m$, $R_e$ is hydrogen, halogen, $C_1$-$C_4$alkyl, —COOR$_j$, trifluoromethyl or methoxy, or $R_d$ and $R_e$ together form a $C_3$-$C_4$alkylene bridge, $R_f$ is hydrogen, halogen or $C_1$-$C_4$alkyl, each of $R_x$ and $R_y$, independently of the other, is hydrogen, halogen, $C_1$-$C_4$alkyl, $C_1$-$C_4$alkoxy, $C_1$-$C_4$alkylthio, —COOR$_4$, trifluoromethyl, nitro or cyano, each of $R_j$, $R_k$ and $R_m$, independently of the others, is hydrogen, or $C_1$-$C_4$alkyl.

3. A compound according to claim 1 wherein $R_b$ is hydrogen.

4. A compound of formula I according to claim 1 wherein the sulfamoyl group occupies the 4-position of the phenyl ring.

5. A compound of formula I according to claim 1 wherein $R_2$ and $R_3$ are hydrogen.

6. A compound of formula I according to claim 1 wherein $R_b$ is hydrogen and the sulfamoyl group occupies the 4-position of the phenyl ring.

7. A compound of formula I according to claim 1 wherein $R_2$, $R_3$ and $R_b$ are hydrogen and the sulfamoyl group occupies the 4-position of the phenyl ring.

8. A compound of formula I according to claim 1 wherein A is the group

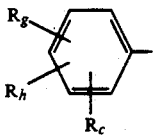

9. A compound of formula I according to claim 8 wherein $R_2$, $R_3$ and $R_b$ are hydrogen and the sulfamoyl group occupies the 4-position of the phenyl ring.

10. A compound of formula I according to claim 1 falling within the scope of subformula Ia

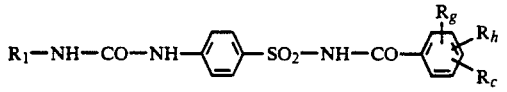
(Ia)

11. A compound of formula Ia according to claim 10 wherein $R_c$ is hydrogen.

12. A compound of formula Ia according to claim 11 wherein $R_1$, $R_g$ and $R_h$ are $C_1$–$C_4$alkyl.

13. 1-[4-(N-4-methylbenzoylsulfamoyl)-phenyl]-3-methylurea according to claim 1.

14. 1-[4-(N-3-methylbenzoylsulfamoyl)-phenyl]-3-methylurea according to claim 1.

15. 1-[4-(N-4-tert.-butylbenzoylsulfamoyl)-phenyl]-3-methylurea according to claim 1.

16. 1-[4-(N-3-trifluoromethylbenzoylsulfamoyl)-phenyl]-3-methylurea according to claim 1.

17. 1-[4-(N-4-nitrobenzoylsulfamoyl)-phenyl]-3-methylurea according to claim 1.

18. 1-[4-(N-3,4-dimethylbenzoylsulfamoyl)-phenyl]-3-methylurea according to claim 1.

19. 1-[4-(N-3,4-dimethylbenzoylsulfamoyl)-phenyl]-3-methylurea according to claim 1.

20. 1-[4-(N-3,4-dimethylbenzoylsulfamoyl)-phenyl]-3,3-dimethylurea according to claim 1.

21. 1-[4-(N-3,4-dimethylbenzoylsulfamoyl)-phenyl]-3-ethylurea according to claim 1.

22. 1-[4-(N-3,4-dimethylbenzoylsulfamoyl)-phenyl]-3-allylurea according to claim 1.

23. 1-[4-(N-3,4-dimethylbenzoylsulfamoyl)-phenyl]-3-phenylurea according to claim 1.

24. 1-[4-(N-3,5-dimethylbenzoylsulfamoyl)-phenyl]-3-methylurea according to claim 1.

25. 1-[4-(N-3,4-dichlorobenzoylsulfamoyl)-phenyl]-3-methylurea according to claim 1.

26. 1-[4-(N-3,4-dimethoxybenzoylsulfamoyl)-phenyl]-3-methylurea according to claim 1.

27. 1-[4-(N-3,4-dimethoxybenzoylsulfamoyl)-phenyl]-3,3-dimethylurea according to claim 1.

28. 1-[4-(N-2,4,5-trimethoxybenzoylsulfamoyl)-phenyl]-3-methylurea according to claim 1.

29. 1-[4-(N-1-naphthylcarbonylsulfamoyl)-phenyl]-3-methylurea according to claim 1.

30. 1-[4-(N-3-methylbenzoylsulfamoyl)-phenyl]-3,3-dimethylurea according to claim 1.

31. 1-[4-(N-3-trifluoromethylbenzoylsulfamoyl)-phenyl]-3-cyclopropylurea according to claim 1.

32. 1-[3-(N-3,4-dimethylbenzoylsulfamoyl)-phenyl]-3-methylurea according to claim 1.

33. A composition for protecting cultivated plants from the phytotoxic action of sulfonylurea herbicides, chloroacetanilide herbicides, acylcyclohexanedione herbicides or aryloxyphenoxypropionic acid herbicides, which composition comprises an effective amount of a compound of formula I according to claim 1 and an agronomically acceptable carrier.

34. A composition for protecting cultivated plants from the phytotoxic action of sulfonylurea herbicides, chloroacetanilide herbicides or aryloxyphenoxypropionic acid herbicides, which composition comprises an effective amount of a compound of formula I according to claim 1 and an agronomically acceptable carrier.

35. A method for protecting cultivated plants against the harmful effects of sulfonylurea, chloroacetanilide, acylcyclohexanedione or aryloxyphenoxypropionic acid herbicides which comprises treating the plant, the seed or the locus thereof with an effective amount of an N-acyl-sulfamoyl-phenyl urea compound of claim 1.

36. A method for protecting cultivated plants against the harmful effects of sulfonylurea, chloroacetanilide or aryloxyphenoxypropionic acid herbicides which comprises applying to the plant, the seed or the locus thereof an effective amount of an N-acyl-sulfamoyl-phenyl urea compound of claim 1.

* * * * *